US005472965A

United States Patent [19]

Sugimoto et al.

[11] Patent Number: 5,472,965
[45] Date of Patent: Dec. 5, 1995

[54] IMIDAZOLE DERIVATIVES HAVING ANTI-HIV ACTIVITY

[75] Inventors: Hirohiko Sugimoto, Suita; Masaru Ogata, Kobe; Hiroshi Matsumoto, Ibaraki; Ken-ichi Sugita, Kashiwara; Akihiko Sato, Ibaraki; Tamio Fujiwara, Kobe, all of Japan

[73] Assignee: Shionogi & Co., Ltd., Osaka, Japan

[21] Appl. No.: 209,627

[22] Filed: Mar. 14, 1994

Related U.S. Application Data

[62] Division of Ser. No. 3,126, Jan. 12, 1993, Pat. No. 5,326,780.

[30] Foreign Application Priority Data

Jan. 16, 1992 [JP] Japan .......................... 4-5577

[51] Int. Cl.⁶ .................... A01N 43/54; A01N 43/50; A01N 43/58; A01N 43/60; C07D 401/12; C07D 403/12; C07D 403/06; C07D 401/06
[52] U.S. Cl. .................... 514/252; 514/341; 514/269; 514/256; 514/397; 514/376; 514/374; 514/377; 514/365; 514/369; 514/370; 546/278; 544/333; 544/315; 544/316; 544/317; 544/318; 544/238; 544/405; 548/314.4; 548/312.7; 548/233; 548/235; 548/182; 548/183; 548/184; 548/186; 548/189; 548/190; 548/193; 548/198; 548/203; 548/205
[58] Field of Search .................... 514/398, 341, 514/269, 256, 252, 397, 376, 374, 377, 365, 369, 370; 548/323.5, 314.4, 312.7, 233, 235, 182, 183, 184, 186, 189, 190, 193, 198, 203, 205; 546/278; 544/333, 315, 316, 238

[56] References Cited

FOREIGN PATENT DOCUMENTS 0477778 4/1992 European Pat. Off. .
63-150266 6/1988 Japan .

OTHER PUBLICATIONS

Iddon et al., J. Chem. Soc. Perkin Trans. 1, No. 7 (1987) pp. 1445–1451.
Iddon et al., J. Chem. Soc. Perkin Trans. 1, No. 4 (1983) pp. 735–738.
Iddon et al., J. Chem. Soc. Perkin Trans. 1, No. 2 (1983) pp. 279–283.
Iddon et al., J. Chem. Soc. Chem. Commun. No. 21 (1981) pp. 1095–1097: Chemical Abstracts, vol. 96 (1982) p. 750 No. 142762f.
Kaneko et al., Chem. Pharm. Bull. vol. 39 No. 4 (1991) pp. 871–875.
Chemical Abstracts, vol. 115 (1991) p. 988 No. 159603p.
McGee et al., Nucleosides and Nucleotides 9(6) 1990 pp. 815–826.
Alonso et al., J. Med. Chem., vol. 28 No. 6 (1985) pp. 834–838.

Primary Examiner—John M. Ford
Attorney, Agent, or Firm—Wenderoth, Lind & Ponack

[57] ABSTRACT

A novel imidazole derivatives of formula I:

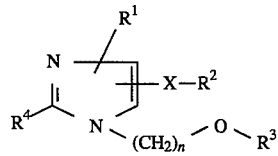

wherein $R^1$ is hydrogen, alkyl, halogen, or optionally substituted aryl; $R^2$ is alkyl, optionally substituted aryl optionally substituted aralkyl, or optionally substituted hetero ring group; $R^3$ is hydrogen, alkyl, optionally substituted aryl, optionally substituted aralkyl, or optionally substituted hydroxyalkyl; $R^4$ is hydrogen, alkyl, halogen, acyl, optionally substituted hydroxyalkyl, optionally esterified or amidated carboxyl group, hydroxy group, aryl or arylthio; X is S, SO, $SO_2$, $CH_2$, or Se; n is an integer of 1 to 3, or a pharmaceutically acceptable salt thereof, said derivative having anti-HIV activity and being useful for the treatment of HIV infections.

4 Claims, No Drawings

IMIDAZOLE DERIVATIVES HAVING ANTI-HIV ACTIVITY

This application is a division of application Ser. No. 08/003,126, filed Jan. 12, 1993 now U.S. Pat. No. 5,326,780.

BACKGROUND OF THE INVENTION

The present invention relates to novel imidazole derivatives, more particularly it relates to novel imidazole derivatives having anti-retrovirus activity and pharmaceutical compositions effective for the treatment of retrovirus infections such as human immunodeficiency syndromes.

AIDS (acquired immunodeficiency syndrome) is caused by a member of retrovirus, human immunodeficiency virus (HIV). In spite of great efforts made by researches, there have been no effective methods for treating AIDS so far and the disease is becoming a more and more serious problem.

It has been reported that pyrimidine nucleoside compounds can be useful anti-retrovirus agents because of the inhibitory activity against the reverse transcription of RNA of retroviruses and many compounds have been synthesized. Among them, azidodeoxythymidine (AZT) has been practically used for treating AIDS. AZT, however, cannot be used broadly due to its high toxicity. Accordingly, the development of anti-HIV compounds which are highly effective and less toxic has been demanded strongly.

It has been reported that acyclovir, an acyclonucleoside derivative, has an inhibitory effect on herpes virus and hence a lot of acyclonucleosides with various side chains were synthesized [J. Heterocyclic Chem. 23, 289 (1986)]. The literature failed to mention about activities against retrovirus.

DETAILED DESCRIPTION OF THE INVENTION

The present inventors have made intensive investigations for the purpose of developing compounds having anti-retrovirus activity and which are useful for the treatment of AIDS and have found that certain imidazole derivatives have such an activity and can prevent HIV infection.

Thus, the present invention provides compounds of the formula I:

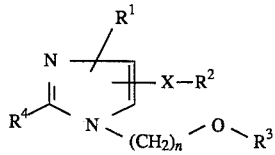

wherein $R^1$ is hydrogen, alkyl, halogen, or optionally substituted aryl; $R^2$ is alkyl, optionally substituted aryl optionally substituted aralkyl, or optionally substituted hetero ring group; $R^3$ is hydrogen, alkyl, optionally substituted aryl, optionally substituted aralkyl, or optionally substituted hydroxyalkyl; $R^4$ is hydrogen, alkyl, halogen, acyl, optionally substituted hydroxyalkyl, optionally esterified or amidated carboxyl group, hydroxy group, aryl or arylthio; X is S, SO, $SO_2$, $CH_2$, or Se; n is an integer of 1 to 3, or a pharmaceutically acceptable salt thereof.

For purposes of the present invention, as disclosed and claimed herein, the following terms are defined below.

The term "alkyl" means a straight or branched saturated hydrocarbon radical having one to ten carbon atoms, preferably, a straight or branched alkyl radical having one to six carbon atoms. Examples of alkyl include methyl, ethyl, n-propyl, i-propyl, n-butyl, i-butyl, s-butyl, t-butyl, n-pentyl, i-pentyl, neopentyl, s-pentyl, t-pentyl, n-hexyl, neohexyl, i-hexyl, s-hexyl, t-hexyl and the like.

For purposes of the present invention, a straight or branched lower alkyl having one to four carbon atoms such as methyl, ethyl, n-propyl, isopropyl or t-butyl is particularly preferred.

The term "halogen" means fluorine, chlorine, bromine and iodine.

The term "acyl" means an aromatic or aliphatic acyl group. Examples of aromatic acyl groups are benzoyl, 4-nitrobenzoyl, 4-tert-butylbenzoyl, benzenesulfonyl, toluenesulfonyl and the like. Examples of aliphatic acyl groups are formyl, acetyl, propionyl, butyryl, valeryl and the like. Aliphatic acyl group is preferred, and formyl is the most preferable group.

The term "aryl" means an aromatic ring group having six to twelve carbon atoms. Examples of aryl group include phenyl, tolyl, xylyl, biphenyl, naphthyl and the like, with the preference of phenyl.

In the definition of "optionally substituted aryl", examples of the substituents include alkyl, halogen, nitro, amino, hydroxy, alkoxy, and aralkyloxy as defined above, with the preference of methyl, fluorine, and chlorine.

The term "hydroxyalkyl" means those derived from an alkyl group as defined above. Preferred hydroxyalkyl groups are hydroxymethyl and hydroxyethyl.

In the definition of "optionally substituted hydroxyalkyl", substituted hydroxyalkyl means those which are derived by substituting an alkyl, aryl, aralkyl or acyl for the hydrogen of the hydroxy group, namely, it includes alkyloxyalkyl, aryloxyalkyl, aralkyloxyalkyl, acyloxyalkyl and the like. Especially, benzyloxyalkyls are preferable.

Examples of "optionally esterified carboxyl group" include carboxyl group, methoxycarbonyl group, ethoxycarbonyl, tert-butoxycarbonyl, benzyloxycarbonyl and the like, with the preference of ethoxycarbonyl.

Salts of compounds of the formula (I) are pharmaceutically acceptable salts formed between a compound (I) and an inorganic acid such as hydrochloric acid, nitric acid, phosphoric acid, sulfuric acid, hydrobromic acid, hydroiodic acid, nitrous acid, phosphorous acid or the like; or a non-toxic organic acid such as aliphatic mono- or dicarboxylic acid, phenyl-substituted alkanoic acid, hydroxy-mono- or hydroxy-di-alkanoic acid, aromatic acid, aliphatic or aromatic sulfonic acid or the like. Examples of pharmaceutically acceptable acid addition salts include sulfate, pyrosulfate, bisulfate, sulfite, bisulfite, nitrate, phosphate, secondary phosphate, primary phosphate, metaphosphate, pyrophosphate, hydrochloride, hydrobromide, hydroiodide, hydrofluoride, acetate, propionate, decanoate, caprylate, acrylate, formate, isobutyrate, caproate, heptanoate, propiolate, oxalate, malonate, succinate, suberate, sebacate, fumarate, maleate, mandelate, butyn- 1,4-dioate, hexyn-1,6-dioate, benzoate, chlorobenzoate, methylbenzoate, dinitrobenzoate, hydroxybenzoate, phthalate, telephthalate, benzenesulfonate, toluenesulfonate, chlorobenzenesulfonate, xylenesulfonate, phenylacetate, phenylpropionate, phenylbutyrate, citrate, lactate, β-hydroxybutyrlate, glycolate, malate, tartrate, methanesulfonate, propanesulfonate, naphthalene-1-sulfonate, naphthalene-2-sulfonate and the like. For purposes of the invention, inorganic salts are preferred, and hydrochloride and nitrate are particularly preferable.

All the compounds (I) as defined above commonly possess the objective anti-retrovirus activity and are useful for the treatment of AIDS. There are certain preferable compounds which have higher anti-HIV activity, e.g., compounds (I) wherein $R^1$ is hydrogen, $C_1$–$C_3$ alkyl, in particular, methyl, ethyl or propyl, halogen, in particular, bromine, or phenyl; $R^2$ is $C_1$–$C_4$ alkyl, in particular, butyl, phenyl, phenyl substituted by halogen or lower alkyl, in particular, dimethylphenyl; $R^3$ is $C_1$–$C_3$ alkyl, in particular, ethyl, benzyl, or hydroxyalkyl, in particular, hydroxyethyl; $R^4$ is hydrogen, $C_1$–$C_3$ alkyl, in particular, methyl or ethyl, halogen, in particular, bromine, formyl, hydroxymethyl, ethoxycarbonyl, carbamoyl, benzyloxymethyl, hydroxyl or phenylthio group; and X is S or $CH_2$ are preferred for purposes of the invention.

As can be understood easily from the formula I, the compounds (I) of the present invention can be in two position isomers in which a substituent of the formula —$CH_2$—O—$R^3$ is attached to either nitrogen atom in the imidazole ring.

The preparation of the compounds (I) of the present invention can be carried out by any of the known methods, for example, those shown by the synthetic routes A, B, C, D, E, F, G, H, and/or I below.

appropriate imidazole derivative, e.g. 4-substituted-imidazole as the starting material. Each reaction can be carried out by employing conditions known to those skilled in the art.

For example, in the first step, an iodine atom is introduced at the 5-position of imidazole ring in the presence of a base in a solvent such as methylene chloride or the like. In the second step, the resultant imidazolyl iodide is added to a mixture of sodium hydride and a solution of thiophenol (or selenophenol) in an appropriate solvent such as dry dimethylformamide to introduce a phenylthio (or phenylseleno) group at the 5-position of imidazole ring. In the third step, a desired substituent, —$(CH_2)_n$—O—$R^3$, is introduced at a nitrogen atom on imidazole ring. This reaction tends to give a mixture of position isomers as a product, in which the group —$(CH_2)_n$—O—$R^3$ is attached to either nitrogen atom at the 1- or 3-positions on imidazole ring. The isomer having the substituent at the desired position can be isolated by any of the conventional methods such as silica gel chromatography. In the fourth step, the imidazole derivatives obtained in steps 1 to 3 above are converted into the objective compound (I). Thus, the hydrogen at the 2-position of Synthetic Route A

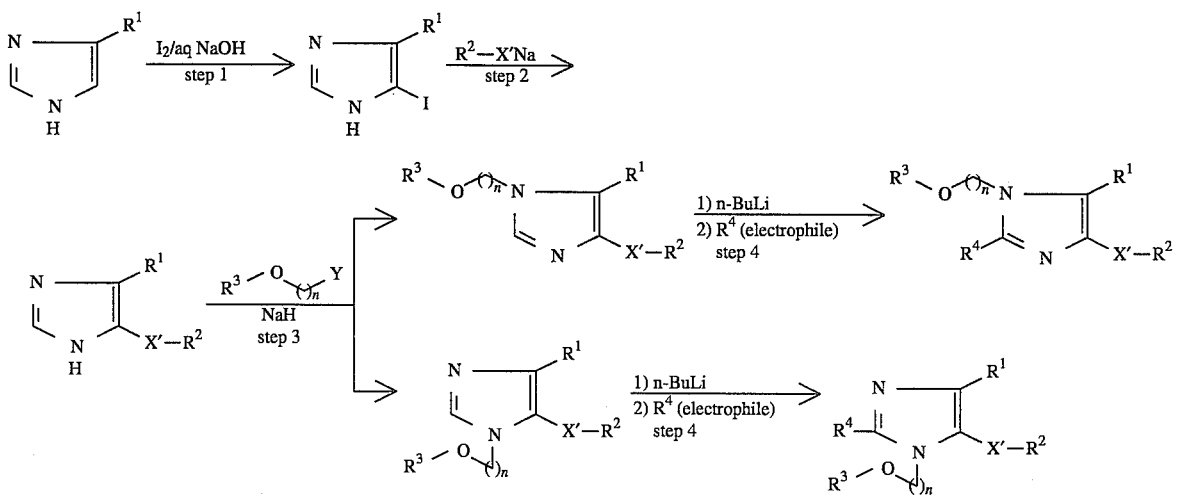

In the reaction scheme above, X' means S or Se and Y means halogen.

The reactions in the synthetic route A can be carried out according to the teachings shown at every step by using an appropriate imidazole ring is replaced by a desired substituent in the presence of an electrophilic reagent known per se in the art, for instance, n-butyllithium.

Synthetic Route B

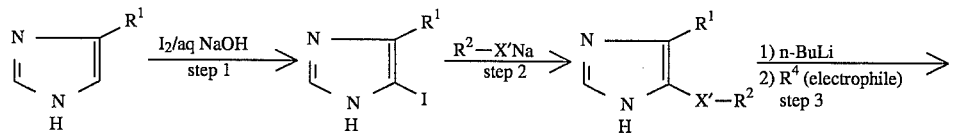

-continued
Synthetic Route B

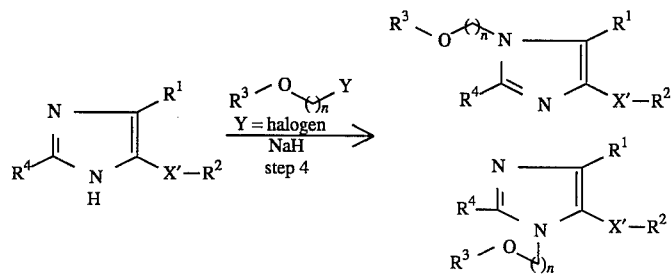

In the reaction scheme above, X' and Y are the same as defined in the Route A. The process is carried out substantially in the same manner as in Route A, except that the substituent $R^4$ is introduced before the introduction of —$CH_2$—O—$R^3$ to the imidazole ring.

Synthetic Route C

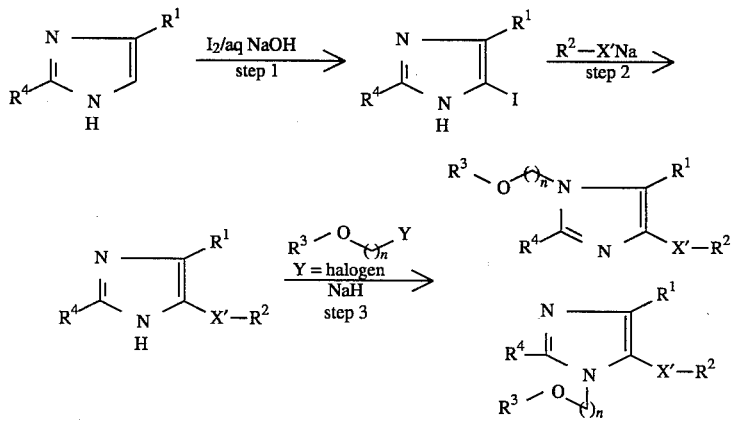

In the reactions scheme above, X' and Y are the same as defined in Routes A and B. This process is carried out substantially in the same manner as in Route A or B, using 2,4-substituted-imidazoles as starting materials. Most of the starting materials are known compounds or, if necessary, they may be readily prepared by conventional reactions.

Synthetic Route D

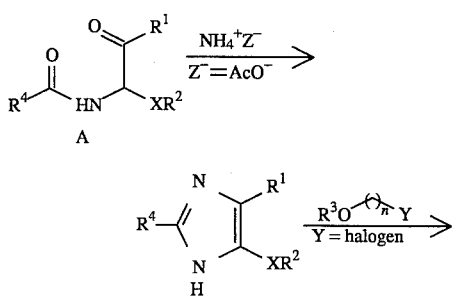

-continued
Synthetic Route D

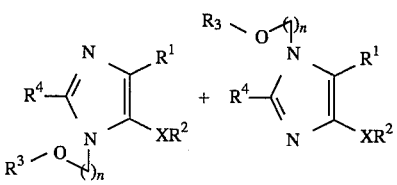

X = S, SO, $SO_2$, Se or $CH_2$?

In the reactions scheme above, $R^1$, $R^2$, $R^3$, $R^4$, and X are the same as defined before.

The starting material A, an α-acylamino-α-substituted-ketone, is refluxed in an organic acid solvent such as actic acid in the presence of ammonia or the salts with organic acids or inorganic acids to give an objective 2,4,5-substituted imidazole. The subsequent reaction may be carried out according to the manner in Route A, B, or C.

The starting material A can be prepared, for example, through either of the following routes.

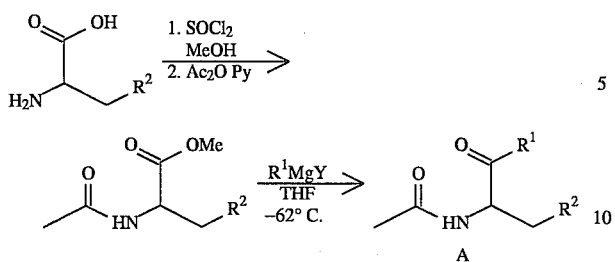

1) X = CH$_2$

Amino acid is halogenated with thionyl halide or phosphorus oxychloride and then refluxed with alkanol to give the ester, which is reacted with an acid anhydride or an activated oganic acid such as acid halide in the presence of a base to give an N-acylamino acid ester. This is treated with a carbanion reagent such as Grignard reagents or organic lithium reagent in an aprotic solvent to give the starting material A.

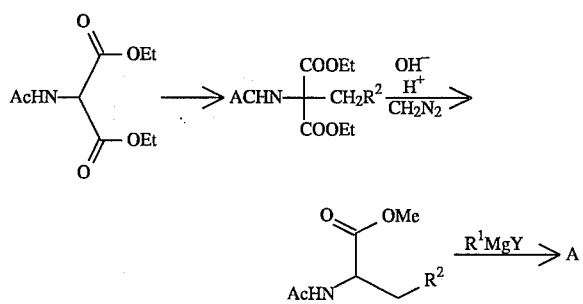

2) X = CH$_2$

Acylaminomalonic acid diester is in the presence of a base alkylated with a substituted methyl halide in an aprotic solvent to give α-aminoacyl-α-substituted malonic acid diester, which is hydrolyzed and decarboxylated, followed by esterification. The resulting ester is treated in the same manner as aforementioned to give the starting material A.

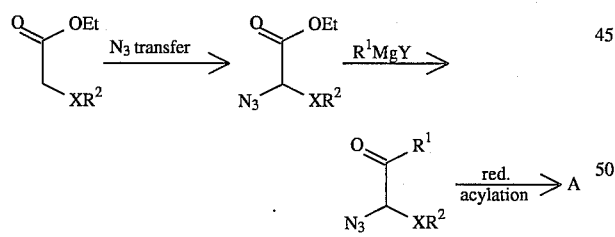

3) X = S, SO, SO$_2$ or Se

A substituted (XR$^2$) acetic acid ester is treated with azide transfer reagent in the presence of a base in an aprotic solvent at a temperature of from −100° C. to room temperature. The azide transfer agent includes, for example, benzenesulfonylazide, 2,4,6-trimethylbenzenesulfonylazide, diphenylphosphorylazide and the like. The reaction mixture is subjected to the same reaction as shown above to give the corresponding ketone. The azide group of the ketone is reduced and acylated to give the starting material A.

Synthetic Route E

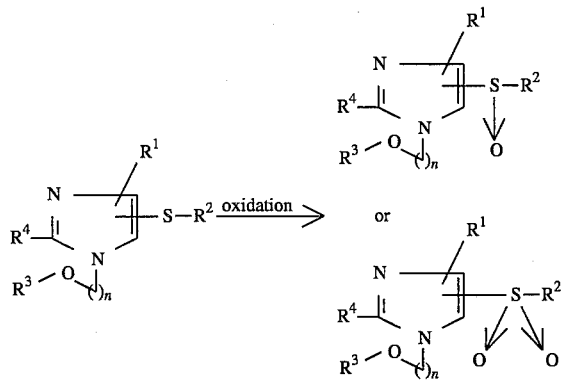

Compounds (I) wherein X is SO or SO$_2$ can be readily obtained by oxidation of the corresponding sulfides. The oxidation is carried out in an appropriate solvent such as methylene chloride, acetonitrile and the like solvent with one or two moles of an appropriate oxidizing agent such as sodium periodate, m-chloroperbenzoic acid, hydrogen peroxide, sodium dichromate, potassium permanganate, chromic acid and the like.

Thus obtained compounds (I) in the synthetic route A, B, C, D or E above may be further modified according to the synthetic route F, G, H, or I as described below to yield desired imidazole derivatives.

Synthetic Route F

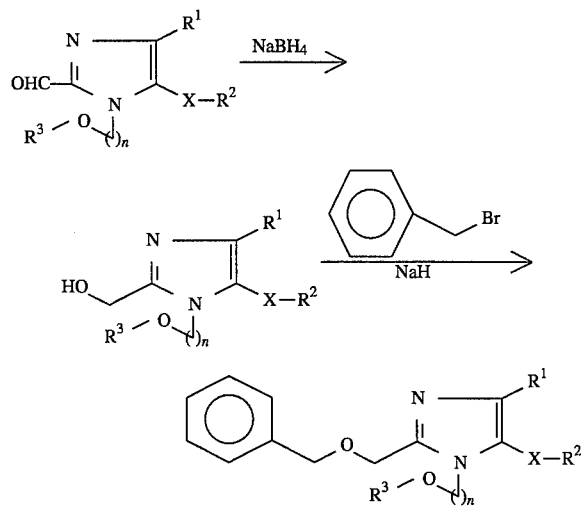

Synthetic Route G

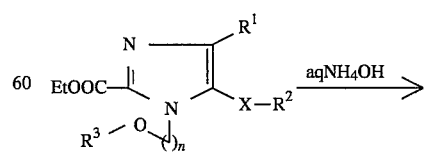

-continued

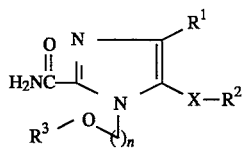

Synthetic Route H

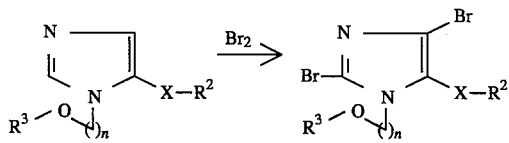

Synthetic Route I

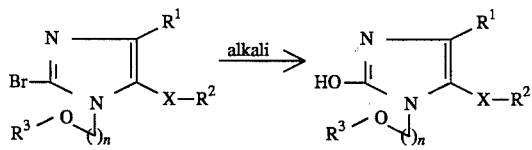

Each reaction in the synthetic routes as noted above is well known to a person skilled in the art and can be effected by applying the well known reaction conditions. In the working Examples as are hereinafter described, specific procedures for each synthetic route are given and one skilled in the art can obtain the compounds of the present invention by employing the same conditions as those used in the Examples or others. For instance, illustrative procedures for each synthetic routes can be seen in the following Examples.

Although the present invention is by no means restricted to the production of a compound (I), there is a certain preferable synthetic route for each compound depending on the definition of "X" in the formula (I) as shown below.

Preferable synthetic routes of compounds (I)

| Synthetic route | X of formula (I) |
| --- | --- |
| A, B, C | S, Se |
| D | S, SO, SO$_2$, Se, CH$_2$ |
| F | S, Se, CH$_2$ |
| G, H, I | S, SO, SO$_2$, Se, CH$_2$ |

As can be seen from the results obtained by experiments described below, the novel compounds (I) of the invention exhibit anti-retrovirus activity in vitro, and can be used in the prevention and/or treatment of HIV (HTLV-IIIB strain) infection.

The compounds of the present invention can be orally or parenterally administered. For oral administration, the compounds of the present invention can be used in any formulations in conventional forms such as solid formulations including tablets, powders, granules, capsules and the like; aqueous solutions; oily suspensions; and liquid formulations including syrups, elixirs and the like. For parenteral administration, the compounds of the present invention can be formulated as aqueous or oily suspension injections. The formulations of the invention can be prepared by using conventional adjuvants such as excipients, binders, lubricants, aqueous solvents, oily solvents, emulsifiers, suspending agents or the like. The formulations may comprise further supplementals such as preservatives, stabilizers or the like.

Appropriate daily dosage of the compounds or salts thereof of the present invention varies depending on various factors such as administration route, age, body weight, conditions and symptoms of the patient to be treated. Generally, the daily dose may be between 0.05–1500 mg, preferably 0.1–500 mg on oral administration, and 0.01–1000 mg, preferably 0.05–300 mg on parenteral administration, said daily dose being administered in 1 to 5 divisions.

The following examples is set forth to further describe the invention but are in no way meant to be construed as limiting the scope thereof.

Example 1

1-Benzyloxymethyl-4-ethyl-2-methyl-5-phenylthio-imidazole

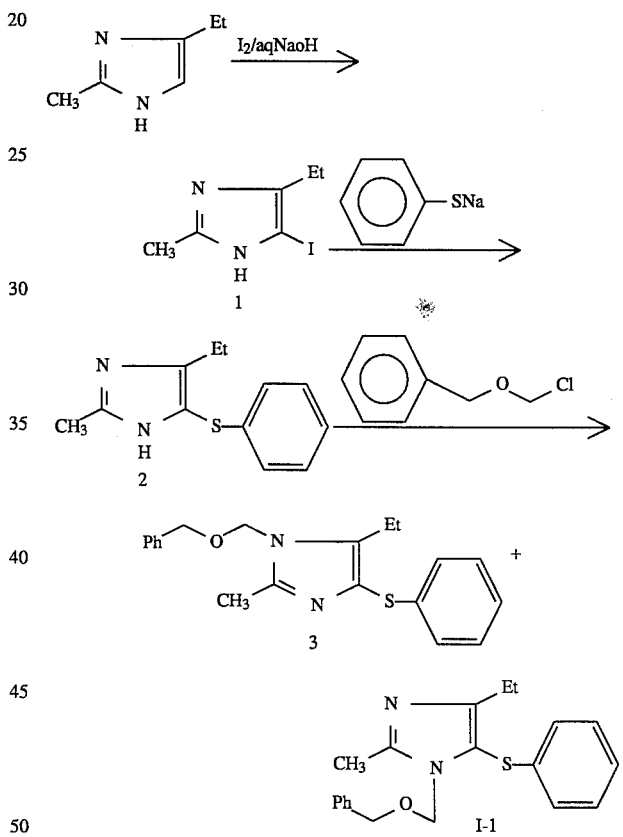

(1) 2-Methyl-4-ethyl-5-iodoimidazole 1

To a solution of 910 mg of NaOH (23 mmol) in 44 ml of water are added 38 ml of methylene chloride and 2.5 g of 2-methyl-4-ethylimidazole (23 mmol). A solution of 5.8 g of iodine (23 mmol) in 44 ml of methylene chloride and 22 ml of methanol is dropwise added under ice cooling. Fifteen minutes later, the mixture is extracted with methylene chloride. The extract is washed with water, dried over NA$_2$SO$_4$, filtered, and the filtrate is concentrated. The resulting crude product is chromatographed on a column of silica gel, eluting with 3% methanol/methylene chloride to give 3.29 g of the desired 2-methyl-4-ethyl-5-iodoimidazole 1. Yield, 62%; mp. 156°–159° C.

1:

$^1$H-NMR(CDCl$_3$-TMS) δppm: 1.19(t,J=7.5 Hz,3H), 2.39(s,3H), 2.57(q,J=7.5 Hz,2H), 9.05(br,1H)

(2) 2-Methyl-4-ethyl-5-phenylthioimidazole 2

To a solution of 2.24 g of thiophenol (20.3 mmol) in 16 ml of dry dimethylformamide is added 1.4 g of sodium hydride (60% oil suspension: 35 mmol) under ice cooling. Ten minutes later, 3.2 g of 2-methyl-4-ethyl-5-iodoimidazole (13.6 mmol) is added to the mixture, which is heated at 130° C. in a nitrogen atmosphere. Two hours later, the dimethylformamide is evaporated in vacuo. The residue is mixed with dry ice and extracted with methylene chloride. The extract is washed with water, dried over $Na_2SO_4$, filtered and the filtrate is concentrated in vacuo. The crude product is chromatographed on a column of silica gel, eluting with 3% methanol/methylene chloride. The product is recrystallized from ethyl acetate/isopropyl ether to give 1.9 g of 2-methyl-4-ethyl-5-phenylthioimidazole 2. Yield, 64%: mp. 171° C.

2:

$^1$H-NMR(CDCl$_3$-TMS) δ ppm: 1.19(t,J=7.5 Hz,3H), 2.39(s,3H), 2.65(q,J7.5 Hz,2H), 5.40(br,1H), 7.03–7.26(m, 5H)

(3) 1-Benzyloxymethyl-5-ethyl-2-methyl-4phenylthioimidazole 3 and 1-benzyloxymethyl-4-ethyl-2-methyl- 5-phenylthioimidazole (I-1)

To a solution of 800 mg of 2-methyl-4-ethyl-5-phenylthioimidazole (3.7 mmol) in 8 ml of dry dimethylformamide is added 220 mg of 60% oil suspension of sodium hydride (5.5 mmol) under ice cooling. Ten minutes later, 860 mg of benzyloxymethyl chloride (5.6 mmol) is added dropwise. Fifteen minutes later, ice water is added to the mixture, which is extracted with ethyl ether. The extract is washed with water, dried over sodium sulfate, filtered and the filtrate is concentrated in vacuo. The residue containing both the non-polar and polar products is chromatographed on a column of silica gel, eluting with ethyl acetate/n-hexane (1:1).

From the former elution is obtained 160 mg of 1-benzyloxymethyl- 5-ethyl-2-methyl-4-phenylthioimidazole 3 as an oil. Yield, 13%.

3:

$^1$H-NMR(CDCl$_3$-TMS) δ ppm: 1.09(t,J=7.4 Hz,3H), 2.43(s,3H), 2.73(q,J=7.4 Hz), 4.52(s,2H), 5.26(s,2H), 7.00–7.31(m,10H)

From the later elution is obtained 810 mg of 1-benzyloxymethyl- 4-ethyl-2-methyl-5-phenylthioimidazole (I-1) as an oil. Yield, 65%. The product, when recrystallized from n-hexane, gives crystals melting at 50°–51° C.

I-1:

$^1$H-NMR(CDCl$_3$-TMS) δ ppm: 1.24(t,J=7.4Hz,3H), 2.53(s,3H), 2.69(q,J=7.4Hz,2H), 4.36(s,2H), 5.30(s,2H), 6.97– 7.31(m,10H)

Elemental analysis ($C_{20}H_{22}N_2OS$) Calcd.(%):C,70.97:H, 6.55:N,8.28:S,9.47 Found (%):C,70.91:H,6.58:N,8.54:S, 9.38

Example 2

1-Ethoxymethyl-4-ethyl-2-methyl-5-phenylthioimidazole (I-2)

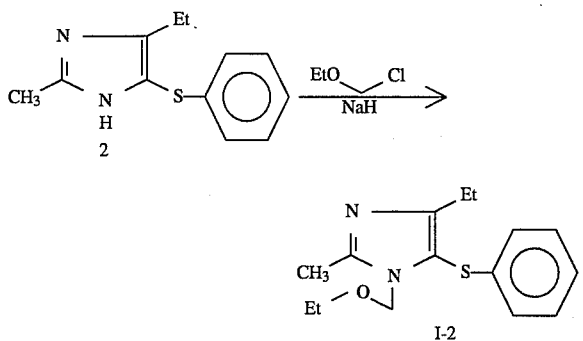

To a solution of 500 mg of 4-ethyl-2-methyl-5-phenylthioimidazole 2 (2.3 mmol) obtained in Example 1 (2) in 5 ml of dry dimethylformamide is added 140 mg of 60% oil suspension of sodium hydride (3.5 mmol) under ice cooling. Five minutes later, 330 mg of ethoxycarbonyl chloride (3.5 mmol) is added to the mixture, which is stirred for 15 minutes. The reaction mixture is poured onto ice water and extracted with ethyl ether. The extract is washed with water, dried over sodium sulfate, filtered and the filtrate is concentrated. The residue is chromatographed on a column of silica gel, eluting with ethyl acetate/n-hexane (2:1) to give 410 mg of the desired product I-2 as an oil. Yield, 65%.

I-2:

$^1$H-NMR(CDCl$_3$-TMS) δ ppm: 1.04(t,J=7.0 Hz,3H), 1.23(t,J=7.4Hz,3H), 2.52(s,3H), 2.68(q,J=7.4 Hz,2H), 3.35 (q,J=7.0 Hz,2H), 5.22(s,2H), 6.98–7.27(m,5H)

Elemental analysis ($C_{15}H_{20}N_2OS$ 1/6H$_2$O) Calcd.(%):C, 64.49:H,7.22:N,10.03:S,11.48 Found (%):C,64.55:H, 7.37:N,10.03:S,11.26

Examples 3–18

In Examples 3 to 18, compounds (I-3)–(I-18) are obtained by conducting the reaction substantially in the same manner as that described in Examples 1 and 2. The resultant compounds are summarized in Table 1 below.

TABLE 1

| Exam No. | X | R$^1$ | R$^2$ | R$^3$ | R$^4$ | mp (°C.) | salt | Comp. No. |
|---|---|---|---|---|---|---|---|---|
| 3 | S | —CH$_3$ | –⟨phenyl⟩ | —CH$_2$–⟨phenyl⟩ | H | 127–128 | HCl | I-3 |

TABLE 1-continued structure:
$$R^4\text{-}C(=N)\text{-}C(R^1)=C(XR^2)\text{-}N(R^3)\text{-}O\text{-}CH_2$$ (ring with R³)

| Exam No. | X | R¹ | R² | R³ | R⁴ | mp (°C.) salt | Comp. No. |
|---|---|---|---|---|---|---|---|
| 4 | S | —C₂H₅ | phenyl | —CH₂-phenyl | H | 129–130 HNO₃ | I-4 |
| 5 | S | H | phenyl | —CH₂-phenyl | H | 145–146 HNO₃ | I-5 |
| 6 | S | phenyl | phenyl | —CH₂-phenyl | H | oil | I-6 |
| 7 | S | —CH₃ | phenyl | —C₂H₅ | H | 79–80 HNO₃ | I-7 |
| 8 | S | —CH₃ | —(CH₂)₃CH₃ | —CH₂-phenyl | H | 124–126 HNO₃ | I-8 |
| 9 | S | —(CH₂)₂CH₃ | phenyl | —CH₂-phenyl | H | 121–122 HNO₃ | I-9 |
| 10 | S | phenyl | phenyl | —CH₂-phenyl | Br | oil | I-10 |
| 11 | S | —CH₃ | phenyl | —C₂H₅ | Br | 90 HNO₃ | I-11 |
| 12 | S | —C₂H₅ | phenyl | —CH₂-phenyl | Br | 53–54 | I-12 |
| 13 | S | —(CH₂)₂CH₃ | phenyl | —CH₂-phenyl | Br | 131–132 HCl | I-13 |
| 14 | S | —C₂H₅ | 3,5-dimethylphenyl | —CH₂-phenyl | —CH₃ | oil | I-14 |
| 15 | S | —C₂H₅ | 3,5-dimethylphenyl | —C₂H₅ | —CH₃ | oil | I-15 |

TABLE 1-continued

| Exam No. | X | R¹ | R² | R³ | R⁴ | mp (°C.) salt | Comp. No. |
|---|---|---|---|---|---|---|---|
| 16 | S | 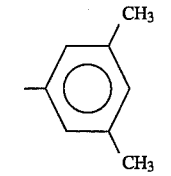 | 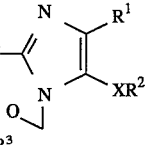 |  | —CH₃ | oil | I-16 |
| 17 | S |  |  | 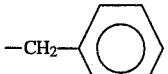 | —CH₃ | 92.5–93.5° | I-17 |
| 18 | S |  |  | —C₂H₅ | —CH₃ | 107~108° HCl | I-18 |

Physicochemical properties of each compound as described in Table 1 are provided below.

I-3:
¹H-NMR(CDCl₃-TMS) δ ppm: (free base)2.36(s,3H), 4.37(s,2H), 5.32(s,2H), 6.97.31(m,10H), 7.82(s,1H)
Elemental analysis (C₁₈H₁₈N₂OS HCl) Calcd.(%):C, 62.33:H,5.52:Cl,10.22:N,8.06:S,9.24 Found (%):C,62.07:H, 5.59:Cl,10.24;N,8.02:S,9.03

I-4:
¹H-NMR(CDCl₃-TMS) δ ppm: 1.25(t,J=7.5 Hz,3H), 2.72 (q,J=7.5 Hz,2H), 4.38(s,2H), 5.32(s,2H), 6.97–7.31(m, 10H), 7.82(s,1H)
Elemental analysis(C₁₉H₂ON₂OS HNO₃) Calcd.(%):C, 58.90:H5.46:N,10.85:S,8.28 Found (%):C,58.88:H5.55:N, 10.93:S,8.35

I-5:
¹H-NMR(CDCl₃-TMS) δ ppm: (free base) 4.36(s,2H), 5.35(s,2H), 7.07.32(m,10H), 7.47(s,1H), 7.89(s,1H)

I-6:
¹H-NMR(CDCl₃-TMS) δ ppm: 4.50(s,2H), 5.27(s,2H), 7.10–7.44 (m,15H), 7.82(s,1H)

I-7:
¹H-NMR CDCl₃-TMS) δ ppm: (free base) 1.02(t,J=7.0 Hz,3H), 2.43(q,j=7.0 Hz,2H), 5.26(s,2H), 6.95–7.27 (m,5H), 7.79(s,1H)
Elemental analysis(C₁₃H₁₆N₂OS HNO₃) Calcd.(%):C, 50.15:H,5.50:N,13.50:S,10.30 Found (%):C,50.09:H, 5.50:N,13.61:S,10.22

I-8:
¹H-NMR(CDCl₃-TMS) δ ppm: 0.86(t,j=7.5H,3H), 1.41(m,4H), 2.33(s,3H), 2.59(t,J=7.5 Hz,2H), 4.48(s,2H), 5.40(s,2H), 7.26–7.35(m,5H), 7.69(s,1H)
Elemental analysis(C₁₆H₂₂N₂OS HNO₃) Calcd.(%):C, 54.37:H,6.56:N,11.89:S,9.07 Found (%):C,54.20:H,6.54:N, 11.78:S,8.92

I-9:
¹H-NMR(CDCl₃-TMS) δ ppm: (free base) 0.95(t,J=7.2 Hz,3H), 1.30.80(m,2H), 2.69(t,J=7.4 Hz,2H), 4.39(s,2H), 5.32(s,2H), 6.97–7.32(m,10H), 7.89(s,1H)
Elemental analysis(C₂₀H₂₂N₂OS HNO₃) Calcd.(%):C, 59.83:H,5.77:N,10.47:S,7.99 Found (%):C,59.66:H,5.72:N, 10.32:S,7.87

I-10:
¹H-NMR(CDCl₃-TMS) δ ppm: 4.54(s,2H), 5.26(s,2H), 7.18–7.42 (m,15H)

I-11:
¹H-NMR(CDCl₃-TMS) δ ppm: (free base) 1.02(t,J=7.0 Hz,3H), 2.32(s,3H), 3.41(q,J=7.0 Hz,2H), 5.29(s,2H), 6.99–7.26(m,5H)
Elemental analysis(C₁₃H₁₅BrN₂OS HNO₃) Calcd.(%):C, 40.01:H,4.13:Br,20.48:N,10.77:S,8.22 Found (%):C, 39.86:H,4.21:Br,20.61:N,10.61:S,8.19

I-12:
¹H-NMR(CDCl₃-TMS) δ ppm: (free base) 1.23(t,J=7.5 Hz,3H), 2.69(q,J=7.5 Hz,2H), 4.47(s,2H), 5.36(s,2H), 6.99–7.31(m,10H)
Elemental analysis(C₁₉H₁₉BrN₂OS) Calcd.(%):C, 56.58:H,4.75:Br,19.81:N,6.95:S,7.95 Found (%):C,56.66:H, 4.77:Br,19.62:N,7.04:S,7.84

I-13:
¹H-NMR(CDCl₃-TMS) δ ppm: (free base) 0.92(t,7.2 Hz,3H), 1.67(m,2H), 2.63(m,2H), 4.56(s,2H), 5.35(s,2H), 7.00–7.30 (m,10H)
Elemental analysis(C₂₀H₂₁BrN₂OS HCl) Calcd.(%):C, 52.93:H,4.89:Br,17.61:Cl,7.81:N,6.17:S, 7.07 Found (%):C, 52.73:H,4.88:Br,17.57:Cl,7.75:N,6.14:S, 7.14

I-14
¹H-NMR(CDCl₃-TMS) δ ppm: 1.24(t,J=7.4 Hz,3H), 2.20(s,6H), 2.52(s,3H), 2.68(q,J=7.4 Hz,2H), 4.37(s,2H), 5.30(s,2H), 6.60–6.74(m,3H), 7.10–7.30(m,5H)

I-15:
¹H-NMR(CDCl₃-TMS) δ ppm: 1.06(t,J=7.0 Hz,3H), 1.24 (t,J=7.4 Hz,2H), 2.22(s,6H), 2.53(s,3H), 2.67(q,J=7.4 Hz,2H), 3.36(q,J=7.0 Hz,2H), 5.23(s,2H)

I-16:
¹H-NMR(CDCl₃-TMS) δ ppm: 1.27(d,J=7.2 Hz,6H), 2.20(s,6H), 2.53(s,3H), 3.18(sept,1H), 4.38(s,2H), 5.30(s, 2H), 6.60–6.74 (m,3H), 7.12–7.31(m,5H)
Elemental analysis(C₂₃H₂₈N₂OS 2/3H₂O) Calcd.(%):C, 70.37:H,7.53:N,7.13:S,8.17 Found (%):C,70.34:H,7.31:N, 7.21:S,7.89

I-17:

¹H-NMR(CDCl₃-TMS) δ ppm: 1.26(d,J=6.8 Hz,6H), 2.52(s,3H), 3.17(sept,1H), 4.37(s,2H), 5.29(s,2H), 6.96–7.30(m,10H)

Elemental analysis(C₂₁H₂₄N₂OS) Calcd.(%):C,71.75:H,6.86:N,7.95:S,9.10 Found (%):C,71.47:H,6.88:N,7.84:S,8.86

I-18:

¹H-NMR(CDCl₃-TMS) δ ppm: 1.03(t,J=7.0 Hz,3H), 1.25 (d,J=7.0 Hz,6H), 2.53(s,3H), 3.17(sept,1H), 3.35 (q,J=7.0 Hz,2H), 5.22(s,2H), 6.95–7.27(m,5H)

Elemental analysis(C₁₆H₂₂H₂OS HCl 1/3H₂O) Calcd.(%):C,57.73:H,7.17:Cl,10.65:N,8.42:S,9.63 Found (%):C,57.92:H,7.13:Cl,10.70:N,8.62:S,9.56

Example 19

1-benzyloxymethyl-2,4-diethyl-5-phenylthioimidazole (I-19)

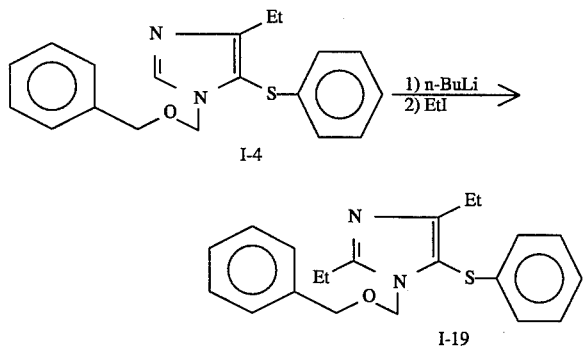

In a mixture of 5 ml of dry tetrahydrofuran and 2.5 ml of dry hexamethylphosphoric triamide is dissolved 150 mg of 1-benzyloxymethyl-4-ethyl-5-phenylthioimidazole (I-4) (0.46 mmol) obtained in Example 4, and the resulting solution is chilled at −78° C. To the solution is added dropwise 1.64M n-butyl lithium solution in 0.49 ml of hexane (0.8 mmol). Five minutes later, 110 mg of ethyl iodide (0.8 mmol) is added to the mixture, which mixture is allowed to stand for 10 minutes, when it is poured onto ice water and extracted with ethyl ether. The extract is washed with water, dried over sodium sulfate and filtered. The filtrate is chromatographed on a column of silica gel, eluting with ethyl acetate/n-hexane (1:2) to give 50 mg of the product (I-19) as an oil. Yield, 31%.

I-19:

¹H-NMR(CDCl₃-TMS) δ ppm: 1.20(t,J=7.4 Hz,3H), 1.37 (t,J=7.4 Hz,3H), 2.71(q,J=7.4 Hz,2H), 2.83(q,J=7.4 Hz,2H), 4.36(s,2H), 5.31(s,2H), 6.96–7.29(m,10H)

Example 20

1-Benzyloxymethyl-2-bromo-4-methyl-5-phenyl-thioimidazole (I-20)

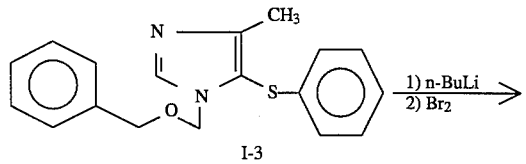

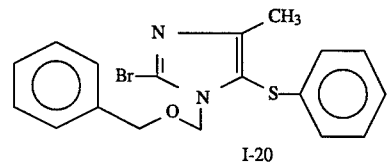

In 5 ml of dry tetrahydrofuran is dissolved 300 mg of 1-benzyloxymethyl-4-methyl-5-phenylthioimidazole (I-3) (1 mmol) obtained in Example 3, and the resulting solution is chilled at −78° C. To the solution is added dropwise 1.64M solution of n-butyl lithium in 0.71 ml of hexane (1.16 mmol) and the mixture allowed to stand for 10 minutes, when 185 mg of bromine (1.16 mmol) is added thereto. Fifteen minutes later, the mixture is poured onto ice water. The mixture is neutralized with sodium bicarbonate and extracted with ethyl ether. The extract is washed with water, dried over sodium sulfate, filtered and the filtrate is concentrated. The crude product is chromatographed on a column of silica gel, eluting with ethyl acetate/n-hexane (1:2) to give 360 mg of the product (I-20; mp. 55° C.). Yield, 96%.

I-20:

¹H-NMR(CDCl₃-TMS) δ ppm: 2.33(s,3H), 4.45(s,2H), 5.36(s,2H), 6.99–7.30(m,10H)

Elemental analysis(C₁₈H₁₇BrN₂SO) Calcd.(%):C,55.53:H,4.40:Br,20.53:N,7.20:S,8.24 Found (%):C,55.56:H,4.53:Br,20.26:N,7.37:S,8.31

Example 21

1-Benzyloxymethyl-2-formyl-4-methyl-5-phenyl-thioimidazole hydrochloride (I-21)

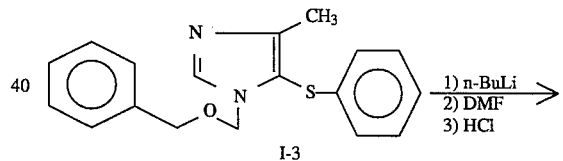

In 5 ml of dry tetrahydrofuran is dissolved 300 mg of 1-benzyloxymethyl-4-methyl-5-phenylthioimidazole (I-3) (1 mmol), and the solution is chilled at −78° C. To the solution is added dropwise 1.64M solution of n-butyl lithium in 0.71 ml of hexane (1.16 mmol) and the mixture allowed to stand for 10 minutes, when 85 mg of dimethylformamide (1.16 mmol) is added thereto. Fifteen minutes later, the mixture is poured onto ice water. The mixture is extracted with ethyl ether. The extract is washed with water, dried over sodium sulfate and concentrated. The crude product is chromatographed on a column of silica gel, eluting with ethyl acetate/n-hexane (1:2) to give 194 mg of the product (I-21) as an oil. Yield, 59%. This product is treated with hydrochloric acid/ethyl ether to give the hydrochloride as crystals melting at 97°–98 ° C.

I-21:

$^1$H-NMR(CDCl$_3$-TMS) δ ppm: 2.35(s,3H), 4.53(s,2H), 5.88(s,2H), 7.02–7.29(m,10H), 9.81(s,1H), IR(film): 1691, 1454, 1112, 1086 cm$^{-1}$ Elemental analysis(C$_{19}$H$_{18}$N$_2$O$_2$S HCl H$_2$O)
Calcd.(%):C,58.08:H,5.39:Cl,9.02:N,7.13:S,8.16
Calcd.(%):C,57.85:H,5.46:Cl,8.66:N,7.09:S,7.97

Example 22

1-Benzyloxymethyl-2-ethoxycarbonyl-4-methyl-5-phenylthioimidazole nitrate (I-22)

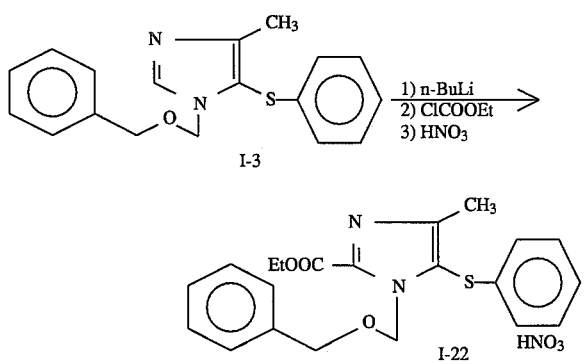

In 10 ml of dry tetrahydrofuran is dissolved 300 mg of 1-benzyloxymethyl-4-methyl-5-phenylthioimidazole (I-3) (1 mmol) obtained in Example 3, and the solution is chilled at −78° C. To the solution is added dropwise 1.64M solution of n-butyl lithium in 0.88 ml of hexane (1.44 mmol) and the mixture is allowed to stand for 10 minutes, when 157 mg of ethyl chloroformate (1.44 mmol) is added thereto. Thirty minutes later, the mixture is poured onto ice water and extracted with ethyl ether. The extract is washed with water, dried over sodium sulfate and filtered. The filtrate is concentrated, and the crude product is chromatographed on a column of silica gel, eluting with ethyl acetate/n-hexane (1:1). The product is treated with nitric acid/ethyl ether to give 71 mg of the product (I-22) as crystals melting at 90°–91° C. Yield, 17%.

I-22:

$^1$H-NMR(CDCl$_3$-TMS) δ ppm: (free base) 1.45(t,J=7.0 Hz,3H), 2.36(s,3H), 4.45(q,J=7.0 Hz,2H), 4.51(s,2H), 5.90(s,2H), 6.97–7.28(m,10H), IR(film):1712,1474,1237 cm$^{-1}$ Elemental analysis (C$_{21}$H$_{22}$N$_2$O$_3$S HNO$_3$) Calcd.(%):C, 56.62:H,5.20:N,9.43:S,7.20 Found (%):C,56.79:H,5.29:N, 9.42:S,7.28

Example 23

2,5-Bis-phenylthio-1-benzyloxymethyl-4-methylimidazole (I-23)

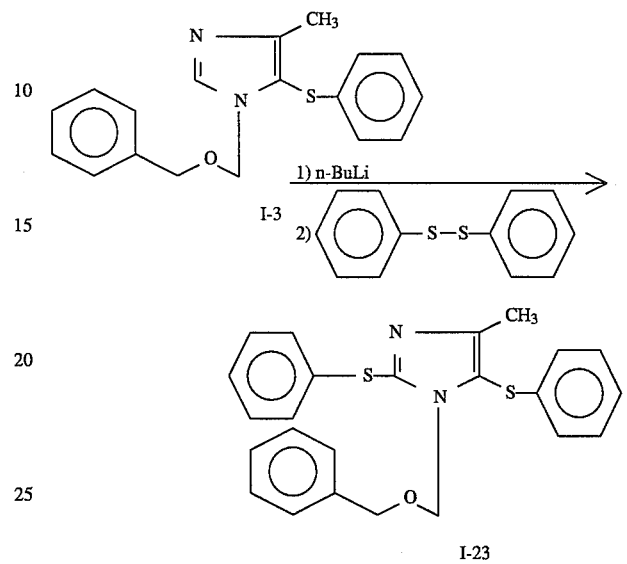

In 6 ml of dry tetrahydrofuran is dissolved 200 mg of 1-benzyloxymethyl-4-methyl-5-phenylthioimidazole (I-3) (0.64 mmol), and the solution is chilled at −78° C. To the solution is added dropwise 1.64M solution of n-butyl lithium in 0.6 ml of hexane (0.98 mmol) and the mixture is allowed to stand for 10 minutes, when 211 mg of diphenyl disulfide (9.7 mmol) is added thereto. Thirty minutes later, the mixture is poured onto ice water. The mixture is extracted with ethyl ether. The extract is washed with water, dried over sodium sulfate, filtered and the filtrate is concentrated. The crude product is chromatographed on a column of silica gel, eluting with ethyl acetate/n-hexane (1:2) to give 250 mg of the product (I-23) as an oil. Yield, 93%.

I-23:

$^1$H-NMR(CDCl$_3$-TMS) δ ppm: 2.38(s,3H), 4.38(s,2H), 5.46(s,2H), 6.98–7.31(m,15H)

Example 24

1-Benzyloxymethyl-2-hydroxymethyl-4-methyl-5-phenylthioimidazole (I-24)

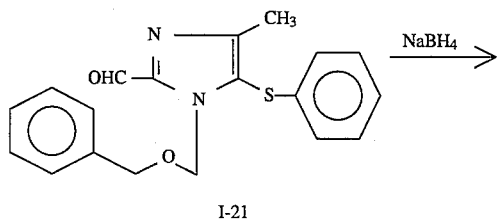

-continued

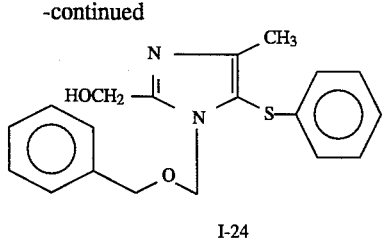

I-24

To a solution of 130 mg of 1-benzyloxymethyl-2-formyl-4-methyl-5-phenylthioimidazole (I-21) (0.38 mmol), obtained in Example 21, in 5 ml of methyl alcohol is added 50 mg of sodium borohydride (1.3 mmol) under ice cooling and the mixture is allowed to stand for 10 minutes, when acetic acid is added thereto. The mixture is neutralized with sodium bicarbonate and extracted with methylene chloride. The extract is washed with water, dried over sodium sulfate, filtered and the filtrate is concentrated. The residue is chromatographed on a column of silica gel, eluting with 2% methanol/ethyl acetate to give 124 mg of the product (I-24). Yield, 94%; mp. 87°–88° C.

I-24:

$^1$H-NMR(CDCl$_3$-TMS) δ ppm: 2.32(s,3H), 3.00(brs.,1H), 4.37(s,2H), 4.79(s,2H), 5.44(s,2H), 6.97.30(m,10H), IR(film) 3172, 1475, 1454, 1438, 1074 cm$^{-1}$ Elemental analysis (C$_{19}$H$_{20}$N$_2$O$_2$S) Calcd.(%):C,67.03:H,5.92:N,8.22:S,9.42 Found (%):C,66.83:H,6.05:N,8.31:S,9.33

Example 25

1,2-Bis-benzyloxymethyl-4-methyl-5-phenylthioimidazole (I-25)

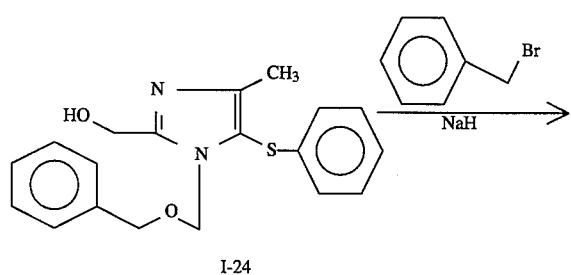

I-24

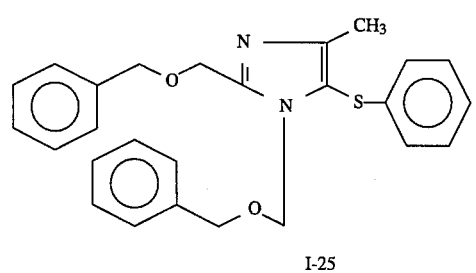

I-25

To a solution of 20 mg of 1-benzyloxymethyl-2-hydroxymethyl- 4-methyl-5-phenylthioimidazole (I-24) (0.06 mmol), obtained in Example 24, in 1 ml of dry dimethylformamide is added 4 mg of 60% oil suspension of sodium hydride (0.1 mmol) under ice cooling. Five minutes later, 15 mg of benzyl bromide (0.09 mmol) is added to the mixture, which is stirred at room temperature for 15 minutes. The mixture is poured onto ice water and extracted with ethyl ether. The extract is washed with water, dried over sodium sulfate, filtered and the filtrate is concentrated. The residue is chromatographed on a column of silica gel, eluting with ethyl acetate/n-hexane (1:1) to give 25 mg of the product (I-25) as an oil. Yield, 95%.

I-25:

$^1$H-NMR(CDCl$_3$-TMS) δ ppm: 2.37(s,2H), 4.34(s,2H), 4.58(s,2H), 4.75(s,2H), 5.47(s,2H), 7.00–7.33(m,15H)

Example 26

1-Benzyloxymethyl-2-carbamoyl-4-methyl-5-phenylthioimidazole (I-26)

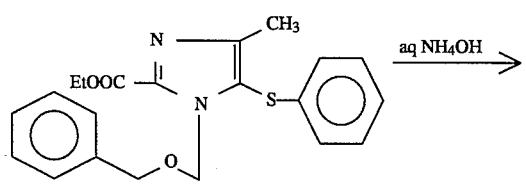

I-22

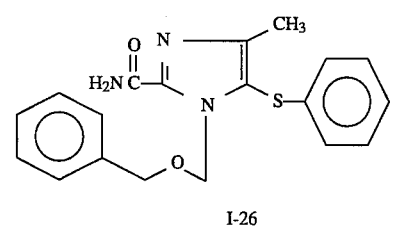

I-26

To a mixture of 10 ml of liquid ammonia and 1 ml of water in a sealing tube is added 200 mg of 1-benzyloxymethyl- 2-ethoxycarbonyl-4-methyl-5-phenylthioimidazole (I-22) (0.5 mmol) obtained in Example 22 and the mixture is heated at 70° C. for 3 hours. After evaporating the ammonia, the residue is chromatographed on a column of silica gel, eluting with ethyl acetate and n-hexane (1:1) to give 111 mg of desired product (I-26). Yield, 60%; mp. 153°–154° C.

I-26:

$^1$H-NMR(CDCl$_3$-TMS) δ ppm: 2.30(s,3H), 4.56(s,2H), 5.49(brs.,1H), 6.00(s,2H), 6.99.–7.30 (m,11H), IR(Nujol) 3338, 3208, 1657 cm$^{-1}$ Elemental analysis(C$_{19}$H$_{19}$N$_3$O$_2$S) Calcd.(%):C,64.57:H,5.42:N,11.89:S,9.07 Found (%):C,64.51:H,5.49:N,11.89:S,9.04

Example 27

1-Benzyloxymethyl-2,4-dibromo-5-phenylthioimidazole (I-27)

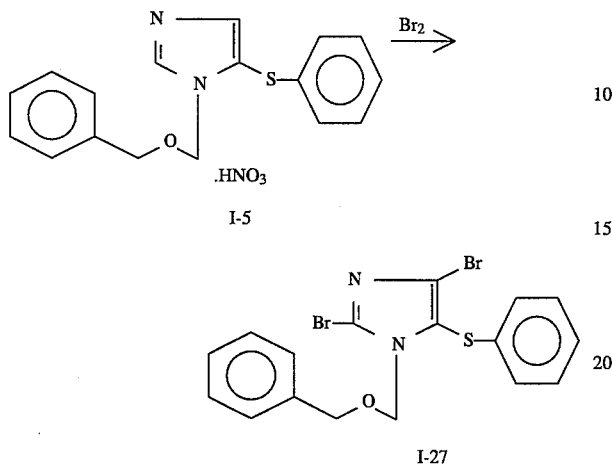

To a solution of 50 mg of 1-benzyloxymethyl-5-phenylthioimidazole nitrate (I-5) (0.14 mmol), obtained in Example 5, in 2 ml of acetic acid is added 70 mg of bromine (0.43 mmol), and the mixture is stirred at room temperature for 1 hour and poured onto ice water. The resultant mixture is neutralized with sodium bicarbonate and extracted with methylene chloride. The extract is washed with water, dried over sodium sulfate, filtered and the filtrate is concentrated. The residue is chromatographed on a column of silica gel, eluting with ethyl acetate/n-hexane (3:1) to give 49 mg of the product (I-27). Yield, 64%; mp. 89°–90° C.

I-27:
$^1$H-NMR(CDCl$_3$-TMS) δ ppm: 4.45(s,2H), 5.43(s,2H), 7.00–7.30 (m,10H)

Example 28

1-Benzyloxymethyl-2-hydroxy-4-methyl-5-phenylthioimidazole (I-28)

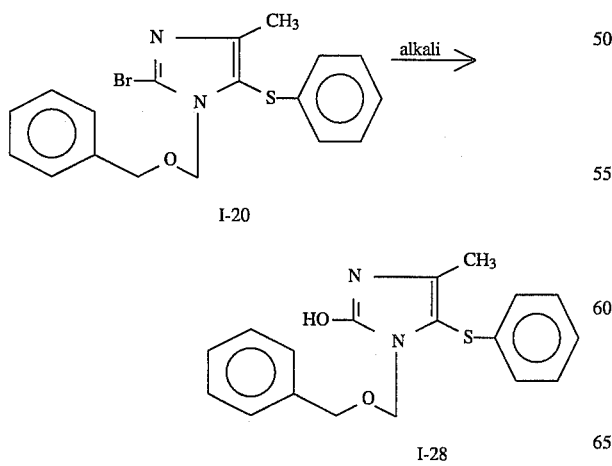

To a mixture of 15 mg of 1-benzyloxymethyl-2-bromo-4-methyl-5-phenylthioimidazole (I-20) (0.04 mmol), obtained in Example 20, and 3 ml of 2-methoxyethyl ether is added 1 ml of 1M sodium methoxide solution in methanol, and the resultant mixture is heated at 130° C. for 5 hours. After evaporating the 2-methoxyethyl ether, the residue is chromatographed on a column of silica gel, eluting with 3% methanol/methylene chloride. The crude product is recrystallized from ethyl acetate/isopropyl ether to give 9 mg of the product (I-28). Yield, 71%; mp. 147°–148° C.

I-28:
$^1$H-NMR(CDCl$_3$-TMS) δ ppm: 2.22(s,2H), 4.54(s,2H), 5.11(s,2H), 7.11–7.26(m,10H), 9.94(br.,1H), IR(Nujol) 3100, 1686, 1457, 1369 cm$^{-1}$ Elemental analysis(C$_{18}$H$_{18}$N$_2$O$_2$S) Calcd.(%):C,66.23:H,5.56:N,8.58:S,9.82 Found (%):C,66.11:H,5.68:N,8.65:S,9.55

Example 29

5-(3,5-Dimethylphenylthio)-4-ethyl-1-[(2-hydroxyethoxy)-methyl]-2-methylimidazole (I-29)

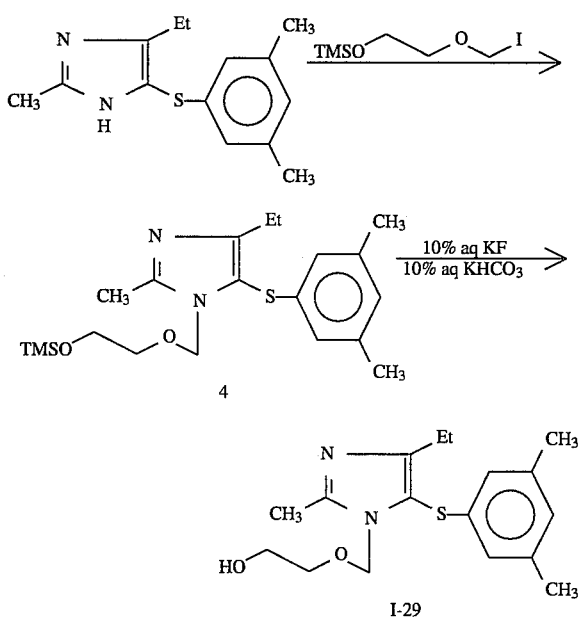

(1) To a solution of 500 mg of 5-(3,5-dimethylphenylthio)- 4-ethyl-2-methylimidazole (2 mmol) in 5 ml of dry dimethylformamide is added 120 mg of 60% oil suspension of sodium hydride (3 mmol) under ice cooling and allowed to stand for 5 minutes. After the addition of 820 mg of iodomethyl trimethylsilyloxyethyl ether (3 mmol) [Tetrahydron Letters, No. 35, pp. 3263–3264, 1979], the mixture is allowed to stand for 15 minutes, when it is poured onto ice water and extracted with ethyl ether. The extract is washed with water, dried over sodium sulfate, filtered and concentrated in vacuo. The residue is chromatographed on a column of silica gel, eluting with ethyl acetate/n-hexane (2:1) to give 170 mg of 5-(3,5-dimethylphenylthio)- 4-ethyl-2-methyl-1-trimethylsilyloxyethoxymethyl-imidazole 4 as an oil. Yield, 21%.

4:

$^1$H-NMR(CDCl$_3$) δ ppm: 0.00(s,9H), 1.27(t,J=7.6 Hz,3H), 2.15(s,6H), 2.67(s,3H), 2.74(q,J=7.6 Hz,2H), 3.28(m,2H), 3.47(m,2H), 5.31(s,2H), 6.54(s,2H), 6.74(s,1H)

(2) Preparation of I-29:

To a mixture of 0.85 ml of 10% aqueous solution of potassium fluoride, 0.85 ml of 10% aqueous solution of potassium bicarbonate and 3.4 ml of dimethylformamide is added 170 mg of 5-(3,5-dimethylphenylthio)-4-ethyl-2-methyl-1-trimethylsilyloxyethoxymethyl-imidazole 4 obtained in (1) above, and the resultant mixture is stirred at room temperature for 30 minutes. The mixture is combined with water and extracted with ethyl ether. The extract is washed with water, dried over sodium sulfate, filtered and concentrated. The residue is chromatographed on a column of silica gel, eluting with 5% methanol/ethyl acetate. The crude product is recrystallized from n-hexane to give 80 mg of the product (I-29) as crystals melting at 87°–89° C. Yield, 58%.

I-29:

$^1$H-NMR(CDCl$_3$-TMS) δ ppm: 1.24(t,J=7.4 Hz,3H), 2.22(s,6H), 2.54(s,3H), 2.69(q,J=7.4 Hz,2H), 5.29(s,2H), 6.61(s,2H), 6.76(s,1H)

Elemental analysis(C$_{17}$H$_{24}$N$_2$O$_2$S) Calcd.(%):C,63.72:H, 7.55:N,8.74:S,10.01 Found (%):C,63.68:H,7.56:N,8.81:S, 9.81

Example 30

5-(2,4-Difluorophenylthio)-4-isopropyl-1-benzyloxymethyl-2-methylimidazole (I-30)

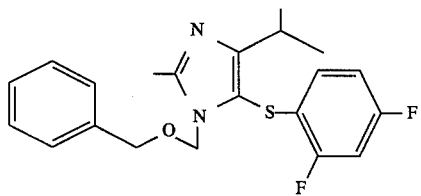

The reaction is effected in the same manner as in Examples 1 and 2 to give the product (I-30).

I-30:

$^1$H-NMR(CDCl$_3$-TMS) δ ppm: 1.23(d,J=7.2 Hz,6H), 2.50(s,3H), 3.18(sept,1H), 4.42(s,2H), 5.32(s,2H), 6.70 . 6.80(m,3H), 7.14.28(m,5H)

Example 31

5-(2,4-Difluorophenylthio)-1-ethoxymethyl-4-isopropyl-2-methylimidazole (I-31) and 4-(2,4-difluorophenylthio)-1-ethoxymethyl-5-isopropyl-2-methyl imidazole (I-86)

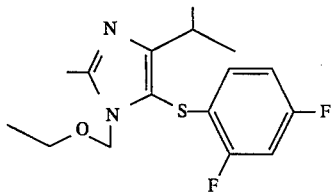

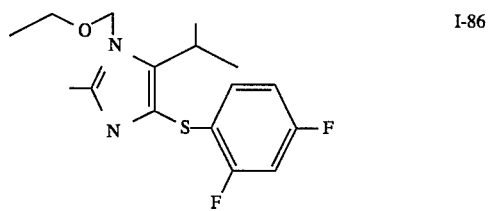

To a solution of 300 mg of 5-(2,4-difluorophenylthio)-4-isopropyl-2-methylimidazole (1.2 mmol) in 3 ml of dry dichloromethane is added 240 mg of triethylamine (2.4 mmol). To the mixture is added dropwise 205 mg of chloromethylehyl ether (2.4 mmol) under ice cooling. After 1-hour-reaction at room temperature, to the reaction mixture is added ice water, which is followed by the addition of aqueous sodium hydrogencarbonate and extraction with methylene chloride. The extract is dried over sodium sulfate, filtered and concentrated in vacuo. The residue containing two products is chromatographed on a column of silica gel, eluting with ethyl acetate/n-hexane (1:1) to separate each product.

The former eluate gives 5 mg of 4-(2,4-difluorophenylthio)- 1-ethoxymethyl-5-isopropyl-2-methyl imidazole (I-86). Yield, 2%.

The later eluate gives 310.0 mg of 5-(2,4-difluorophenylthio)- 1-ethoxymethyl-4-isopropyl-2-methylimidazole (I-31). Yield, 84%.

I-31:

$^1$H-NMR(CDCl$_3$-TMS) δ ppm: 1.05(t,J=7.0 Hz,3H), 1.22 (d,J=7.0 Hz,6H), 2.52(s,3H), 3.17(sept,1H), 3.38 (q,J=7.0 Hz,2H), 5.24(s,2H), 6.70–6.90(m,3H)

I-86:

$^1$H-NMR(CDCl$_3$-TMS) δ ppm: 1.02(t,J=6.8 Hz,3H), 1.22 (d,J=7.0 Hz,6H), 2.52(s,3H), 3.13(sept,1H), 3.35 (q,J=6.8 Hz,2H), 5.21(s,2H), 6.50–7.50(m,3H)

Examples 32–36

In Examples 32 to 36, the reaction is effected in the same manner as in Examples 1–2 to give the products I-32 to I-36 as summarized in Table 2 below.

TABLE 2

Structure:
```
        N      R¹
   R⁴

N      XR²
   R³─O
```

| Example No. | X | R¹ | R² | R³ | R⁴ | mp (°C.) | Compound No. |
|---|---|---|---|---|---|---|---|
| 32 | S | —CH(CH₃)₂ | 3,5-dimethylphenyl (Me, Me) | —C₂H₅ | —CH₃ | mp 169–170° C. (H₂SO₄ salt) | I-32 |
| 33 | S | —CH(CH₃)₂ | 3,5-dimethylphenyl (Me, Me) | —CH₃ | —CH₃ | mp 163–164° C. (H₂SO₄ salt) | I-33 |
| 34 | S | —C(CH₃)₃ | 3,5-dimethylphenyl (Me, Me) | —C₂H₅ | —CH₃ | mp 67–68° C. | I-34 |
| 35 | S | —C(CH₃)₃ | 3,5-dimethylphenyl (Me, Me) | —CH₃ | —CH₃ | mp 74–75° C. | I-35 |
| 36 | S | —C(CH₃)₃ | phenyl | —CH₂-phenyl | —CH₃ | oil | I-36 |

Physicochemical properties of the compounds as described in Table 2 are shown below.

I-32:
$^1$H-NMR(CDCl₃-TMS) δ ppm: 1.26(m,J=7 Hz,6H), 1.65(t,J=7 Hz,3H), 2.12(s,6H), 2.53(s,3H), 3.17(m,J=7 Hz,1H), 3.36(q,J=7 Hz,2H), 5.22(s,2H), 6.59–6.74(m,3H)
Elemental analysis(C₁₈H₂₆N₂OS H₂SO₄) Calcd.:C, 51.90:H,6.77:N,6.73:S,15.40 Found :C,51.78:H,6.78:N, 6.71:S,15.66

I-33:
$^1$H-NMR(CDCl₃-TMS) δ ppm: 1.26(m,J=7 Hz,6H), 2.22(s,6H), 2.52 (s,3H), 3.17(m,J=7 Hz,1H), 3.18(s,3H), 5.18(s,2H), 6.59– 6.74(m,3H)
Elemental analysis(C₁₇H₂₄N₂OS H₂SO₄) Found :C,50.72:H,6.51:N,6.96:S,15.93 Calcd.:C,50.84:H,6.62:N, 6.81:S,15.76

I-34:
$^1$H-NMR(CDCl₃-TMS) δ ppm: 1.05(t,J=7 Hz,3H), 1.39(s,9H), 2.21(s,6H), 3.51(s,3H), 3.38(q,J=7 Hz,2H), 5.17(s,2H), 6.53–6.73(m,3H)
Elemental analysis(C₁₉H₂₈N₂OS H₂S)₄) Calcd.:C, 53.00:H,7.02:N,6.51:S,14.89 Found :C,53.14:H,7.05:N, 6.61:S,14.98

I-35:
$^1$H-NMR(CDCl₃-TMS) δ ppm: 1.39(s,9H), 2.21(s,6H), 2.51(s,3H), 3.20(s,3H), 5.13(s,2H), 6.53–6.73(m,3H)
Elemental analysis(C₁₈H₂₆N₂SO H₂SO₄) Calcd.:C, 51.90:H,6.77:N,6.73:S,15.40 Found :C,51.66:H,6.88:N, 6.66:S,15.33

I-36:
$^1$H-NMR(CDCl₃-TMS) δ ppm: 1.39(s,9H), 2.50(s,3H), 4.39(s,2H), 5.24(s,2H), 6.90–7.30(m,10H)

Example 37

1-Benzyloxymethyl-4-isopropyl-2-methyl-5-phenyl-selenylimidazole (I-37) and 1-benzyloxymethyl-4-phenylselenyl-2-methyl-5-isopropyl-imidazole

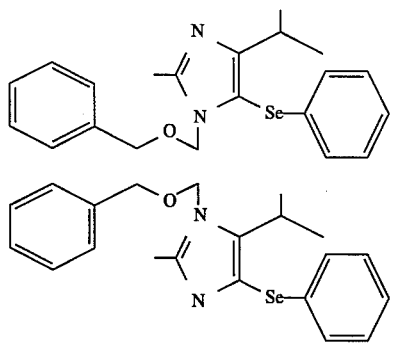

(1) 2-methyl-4-isopropyl-5-phenylselenyl-imidazole and 2-methyl-4-phenylselenyl-5-isopropyl-imidazole To a solution of 960 mg of benzeneselenol (6.0 mol) in 10 ml of dry dimethylformide is added 400 mg of 60% oil suspension of sodium hydride (10 mmol) under ice cooling and the mixture is allowed to stand for 10 minutes. After the addition of 1 g of 2-methyl-4-isopropyl-5-iodoimidazole (4 mmol), the mixture is heated at 140° C. in a nitrogen atmosphere for 1 hour. The resultant mixture is mixed with ice water and dry ice and extracted with diethyl ether. The extract is washed with water, dried over sodium sulfate and filtered. The filtrate is concentrated in vacuo, and the crude product is chromatographed on a column of silica gel, eluting with 3% methanol/methylene chloride. The product is recrystallized from isopropyl ether to give 900 mg of the desired 2-methyl-4-isopropyl-5-phenylselenylimidazole and 2-methyl-4-phenylselenyl-5-isopropylimidazole. Yield 80%; mp. 146°–147° C.

$^1$H-NMR(CDCl$_3$-TMS) δ ppm: 1.24(d,J=7.20 Hz,6H9), 2.41(s,3H), 3.21(sept,1H), 7.18(m,5H)

(2) 1-benzyloxymethyl-4-isopropyl-2-methyl-5-phenyselenylimidazole (I-37) and 1-benzyloxymethyl-2-methyl-4-phenylselenyl- 5-isopropyl-imidazole (I-87).

To a solution of 400 mg of 2-methyl-4-isopropyl-5-phenylselenyl-imidazole (1.4 mmol) in 4 ml of dry dimethylformamide is added 70 mg of 60% oil suspension of sodium hydride (1.8 mmol) under ice cooling and the mixture is allowed to stand for 5 minutes followed by the addition of 270 mg of benzyloxymethyl chloride (1.7 mmol). The mixture is stirred for 30 minutes under ice cooling, mixed with ice water and extracted with diethyl ether. The extract is washed with water, dried over sodium sulfate and filtered. The filtrate is concentrated in vacuo. The crude product is chromatographed on a column of silica gel, eluting with ethyl acetate/n-hexane (1:1). The product is recrystallized from n-hexane to give 297 mg of the objective 2-methyl-4-phenylselenyl-5-isopropyl-imidazole (I-87) and 1-benzyloxymethyl-4-isopropyl-2-methyl-5-phenylselenyl-imidazole (I-37). Yield, 52%; mp. 94°–96° C.

I-37:

$^1$H-NMR(CDCl$_3$-TMS) δ ppm: 1.27(d,J=7.0 Hz,6H), 2.55(s,3H), 3.21(sept,1H), 4.36(s,3H), 5.36(s,2H), 7.10–7.30(m,10H)

Elemental analysis(C$_{21}$H$_{24}$N$_2$OSe) Calcd.(%):C,63.15:H, 6.06:N,7.01 Found (%):C,63.12:H,6.04:N,6.97

I-87:

$^1$H-NMR(CDCl$_3$-TMS) δ ppm: 1.34(t,J=7.0 Hz,6H), 2.53(s,3H), 3.15(sept,1H), 4.54(s,2H), 5.29(s,2H), 7.20–7.50(m,10H)

Example 38

1-Ethoxymethyl-4-isopropyl-2-methyl-5-phenylselenyl-imidazole (I-38)

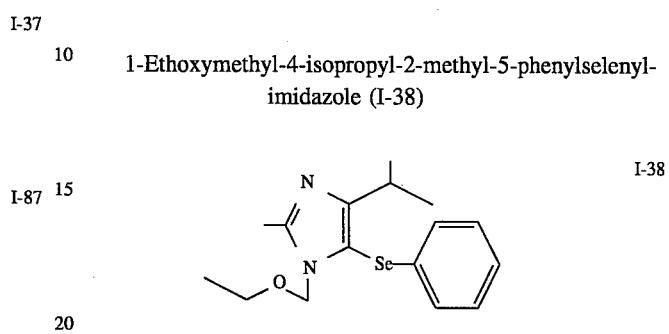

The titled compound (I-38) was prepared as an oil in the same manner as that described in Example 37.

I-38:

$^1$H-NMR(CDCl$_3$-TMS) δ ppm: 1.03(t,J=7.0 Hz,3H), 1.27 (d,J=7.0 Hz,6H), 3.21(sept,1H), 3.34(q,2H), 5.28(s,2H), 7.10–7.26(m,5H)

Example 39

1-(2-Hydroxyethoxymethyl)-4-isopropyl-2-methyl-5-phenylselenyl-imidazole (I-39)

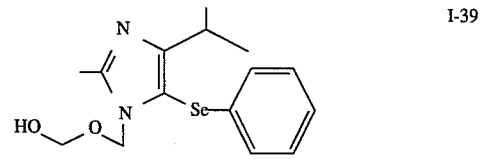

Compound (I-39) was prepared according to the synthetic route B.

To a solution of 560 mg of 2-methyl-4-isopropyl-5-phenylselenyl-imidazole (2 mmol) in 5.6 ml of dry dimethylformamide is added 120 mg of 60% oil suspension of sodium hydride (3 mmol) under ice cooling and the mixture is allowed to stand for 5 minutes. To the mixture is added 820 mg of iodomethyl trimethylsilyloxyethyl ether (3 mmol) and allowed to stand for 10 minutes, when the reaction mixture is poured onto ice water and extracted with ethyl ether. The extract is washed with water, dried over sodium sulfate, filtered and concentrated in vacuo. The residue is chromatographed on a column of silica gel, eluting with ethyl acetate/n-hexane (2:1) to give 70 mg of 1-(2-hydroxyethoxymethyl)-4-isopropyl-2-methyl-5-phenylseleny dazole as an oil. Yield, 10%.

I-39:

$^1$H-NMR(CDCl$_3$-TMS) δ ppm: 1.27(d,J=6.8 Hz,6H), 2.56(s,3H), 2.97(t,J=6.6 Hz,2H), 3.21(sept,1H), 3.52(t,J=6.6 Hz,2H), 5.33(s,2H), 6.90.26(m,5H)

Example 40

1-Benzyloxymethyl-4-isopropyl-2-methyl-5-phenyl-sulfinyl-imidazole (I-40)

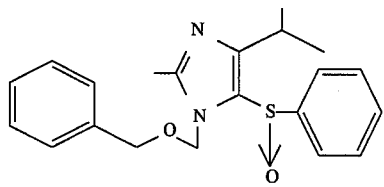

I-40

To a solution of 500 mg of 1-benzyloxymethyl-4-isopropyl-2-methyl-5-phenylthio-imidazole (1.4 mmol) in 10 ml of methylene chloride is added 370 mg of m-chloroperbenzoic acid (2.1 mmol) under ice cooling, and the resultant mixture is stirred at room temperature for 3 hours. The mixture is mixed with aqueous sodium thiosulfate and aqueous sodium hydrogencarbonate and extracted with methylene chloride. The extract is washed with water, dried over sodium sulfate, filtered and concentrated in vacuo. The residue is chromatographed on a column of silica gel, eluting with ethyl acetate/n-hexane (1:1) to give 471 mg of the objective 1-benzyloxymethyl-4-isopropyl-2-methyl-5-phneylsulfinyl-imidazole as crystals melting at mp. 72°–74° C. Yield, 54%.

I-40:

$^1$H-NMR(CDCl$_3$-TMS) δ ppm: 1.36(d,d,J=7.2 Hz,7.0 Hz,6H), 2.38(s,3H),3.33(sept,1H), 4.12(d,J=11.6 Hz,1H), 4.21(d,J=11.6 Hz 1H), 5.18(s,2H), 7.09–7.52(m,10H)

Elemental analysis(C$_{21}$H$_{24}$N$_2$O$_2$S) Calcd.(%):C,68.45:H, 6.57:N,7.60:S,8.70 Found (%):C,68.31:H,6.65:N,7.65:S, 8.47

Example 41

1-Benzyloxymethyl-4-isopropyl-2-methyl-5-phenyl-sulfinyl-imidazole (I-41)

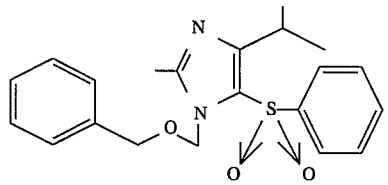

I-41

To a solution of 1 g of 1-benzyloxymethyl-4-isopropyl-2-methyl-5-phenylthio-imidazole (2.8 mmol) in 40 ml of methylene chloride is added 1.84 g of m-chloroperbenzoic acid (10.7 mmol) under ice cooling, and the resultant mixture is stirred at room temperature. Six hours later, the reaction mixture is mixed with aqueous sodium thiosulfate and aqueous sodium hydrogenecarbonate and extracted with methylene chloride. The extract is washed with water, dried over sodium sulfate, filtered and concentrated in vacuo. The residue is chromatographed on a column of silica gel, eluting with ethyl acetate/n-hexane (1:1) to give 580 mg of the objective 1-benzyloxymethyl-4-isopropyl- 2-methyl-5-phenylsulfonyl-imidazole as crystals melting at mp. 116°–117° C. Yield, 53%.

I-41:

$^1$H-NMR(CDCl$_3$-TMS) δ ppm: 1.26(d,J=7.2 Hz,6H), 2.42(s,3H), 3.76(sept,1H), 4.41(s,2H), 5.59(s,2H), 7.17–7.58(m,8H), 7.87–7.91(m,2H)

Elemental analysis(C$_{21}$H$_{24}$N$_2$O$_3$S H$_2$O) Calcd.(%):C, 62.66:H,6.51:N,6.96:S,7.98 Found (%):C,62.73:H,6.25:N, 7.01:S,7.83

Example 42

5-Benzyl-1-benzyloxymethyl-4-isopopyl-2-methylimidazole (I-42).

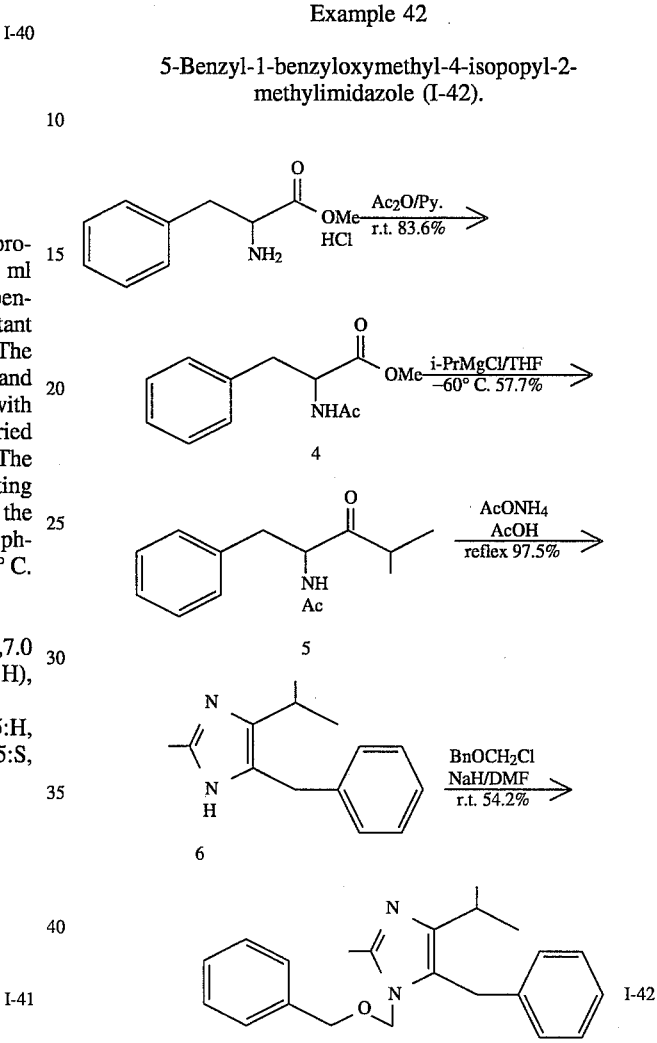

(1) N-acetylphenylalanine methyl ester 4

To a solution of 2.73 g of L-phenylalanine methyl ester hydrochloride (12.7 mmol ) in 5.00 g of pyridine (63.2 mmol) is dropwise added 12.90 g of acetic anhydride (126.0 mmol) under ice cooling. The mixture is allowed to stand for 2 hours and concentrated in vacuo. The residue is extracted with ethyl acetate. The extract is washed with 5% hydrochloric acid, saturated aqueous sodium bicarbonate and saturated brine in order, dried over sodium sulfate, filtered and concentrated in vacuo to give 2.34 g of the objective N-acetylphenylalanine methyl ester 4. Yield, 83.6%.

I-42:

$^1$H-NMR(CDCl$_3$-TMS) δppm: 1.99(s,3H), 3.13(m,2H), 3.73(s,3H), 4.89(m,1H), 5.89(br,1H), 7.06–7.33(m,5H)

Elemental analysis(C$_{12}$H$_{15}$NO$_3$) Calcd.(%);C,65.14:H, 6.83:N,6.33 Found (%);C,65.12:H,6.80:N,6.31

(2) 4-Acetylamino-2-methyl-5-Phenyl-3-pentanone 5

A solution of 2.30 g of N-acetylphenylalanine methyl ester (10.40 mmol) in 15 ml of tetrahydrofuran is chilled at −60° C. with a dry ice/acetone bath. To the mixture is added dropwise 10.40 ml of 2M solution of isopropylmagnesium chloride in tetrahydrofuran (20.8 mmol) with stirring and the mixture allowed to stand for 15 minutes and returned to room temperature. The mixture was stirred for 3 hours. To the mixture is added saturated aqueous ammonium chloride under ice cooling, followed by the addition of 5% hydrochloric acid and the mixture is extracted with ethyl acetate. The extract is washed with saturated brine, dried over sodium sulfate, filtered and the filtrate concentrated in vacuo. The resulting crude product is chromatographed on a column of silica gel, eluting with methylene chloride and ethyl acetate (4:1) to give 1.40 g of the objective 4-acetylamino-2-methyl-5-phenyl- 3-pentanone 5. Yield, 57.7%.

5:

$^1$H-NMR(CDCl$_3$-TMS) δ ppm: 1.00(d,J=6.6 Hz,3H), 1.09(d,J=7.2 Hz,3H), 1.97(s,3H), 2.68(m,1H), 3.04(m,2H), 5.06(m,1H), 6.07(br,1H), 7.08–7.34(m,5H)

Elemental analysis(C$_{14}$H$_{19}$NO$_2$ 0.1H$_2$O) Calcd.(%);C, 71.52:H,8.23:N,5.96 Found (%);C,71.62:H,8.08:N,6.03

(3) 5-Benzyl-4-isopropyl-2-methylimidazole

To a solution of 1.00 g of 4-acetylamino-2-methyl- 5-phenyl-3-pentanone (4.29 mmol) in 20 ml of acetic acid is added 5.00 g of ammonium acetate (64.9 mmol), and the resultant mixture is heated under reflux. One hour later, the reaction mixture is concentrated in vacuo, neutralized with aqueous sodium bicarbonate and extracted with ethyl acetate. The extract is washed with saturated brine, dried over sodium sulfate, filtered and the filtrate is concentrated. The crude product is recrystallized from ether/n-hexane to give 0.90 mg of the objective 5-benzyl-4-isopropyl- 2-methylimidazole 6. Yield, 97.5%.

6:

$^1$H-NMR(CDCl$_3$-TMS) δ ppm: 1.23(d,J=7.0 Hz,6H), 2.29(m,1H), 3.86(s,2H), 7.13–7.31(m,5H)

Elemental analysis(C$_{14}$H$_{18}$N$_2$) Calcd.(%);C,78.46:H, 8.47:N,13.07 Found (%);C,78.20:H,8.50:N,12.89

(4) 5-Benzyl-1-benzyloxymethyl-4-isopropyl-2-methylimidazole (I-42)

To a solution of 980 mg of 5-benzyl-4-isopropyl- 2-methylimidazole (4.58 mmol) in 9.8 ml of dry dimethylformamide is added 238 mg of 60% oil suspension of sodium hydride (5.95 mmol) under ice cooling. Ten minutes later, 935 mg of benzyloxymethyl chloride (5.97 mmol) is dropwise added. One hour later, the reaction mixture is poured onto ice water and extracted with ethyl acetate. The extract is washed with saturated brine, dried over sodium sulfate, filtered and the filtrate is concentrated in vacuo. The crude product is chromatographed on a column of silica gel, eluting with ethyl acetate and n-hexane (1:1) to give 820 mg of the objective 5-benzyl-1-benzyloxymethyl- 4-isopropyl-2-methylimidazole (I-42). Yield, 54.17%.

I-42:

$^1$H-NMR(CDCl$_3$-TMS) δ ppm: 1.28(d,J=6.6 Hz,6H), 2.38(s,3H), 2.93(m,1H), 3.96(s,2H), 4.32(s,2H), 4.96(s,2H), 7.01–7.39(m,10H)

Elemental analysis(C$_{22}$H$_{26}$N$_2$O 0.8H$_2$O) Calcd.(%);C, 75.74:H,7.97:N,8.03 Found (%);C,75.78:H,7.75:N,8.00

Examples 43–70

In Examples 43 to 70, desired compounds (I-43)– (I-70) and (I-88)–(I-95) as shown in the following Tables 3–8 were prepared according to the synthetic route D in the same manner as described in Example 42 above. Among them, compounds (I-88)–(I-95) are position isomers of compounds (I-61), (I-62) and (I-67) -(I-72), respectively. The isomers are separated from each other at an appropriate reaction step of each Example, said step corresponding to Example 42, (2) (i.e., step 2 of synthetic route D). Example 61: compounds I-61 and I-88; Example 62: compounds I-62 and I-89; Example 67: compounds I-67 and I-90; Example 68: compounds I-68 and I-91; Example 69: compounds I-69 and I-92; Example 70: compounds I-70 and I-93; Example 71: compounds I-71 and I-94; and Example 72: compounds I-72 and I-95.

TABLE 3

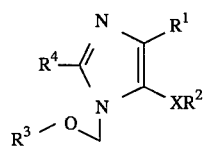

| Example No. | X | R$^1$ | R$^2$ | R$^3$ | R$^4$ | mp (°C.) | Compound No. |
|---|---|---|---|---|---|---|---|
| 43 | CH$_2$ | —CH(CH$_3$)$_2$ | —C$_6$H$_5$ | —CH$_2$CH$_2$OAc | —CH$_3$ | oil | I-43 |
| 44 | CH$_2$ | —CH(CH$_3$)$_2$ | —C$_6$H$_5$ | —C$_2$H$_5$ | —CH$_3$ | mp 60–61° C. | I-44 |
| 45 | CH$_2$ | —CH(CH$_3$)$_2$ | —C$_6$H$_5$ | —CH$_2$CH$_2$OH | —CH$_3$ | mp 130–131° C. | I-45 |
| 46 | CH$_2$ | —CH(CH$_3$)$_2$ | —C$_6$H$_4$—OMe | —CH$_2$—C$_6$H$_5$ | —CH$_3$ | oil | I-46 |

TABLE 3-continued

Structure: $R^4$ and $R^1$ on a ring with N, N—O—$R^3$, and $XR^2$ substituents.

| Example No. | X | $R^1$ | $R^2$ | $R^3$ | $R^4$ | mp (°C.) | Compound No. |
|---|---|---|---|---|---|---|---|
| 47 | $CH_2$ | $-CH(CH_3)_2$ | 4-MeO-C₆H₄- | $-C_2H_5$ | $-CH_3$ | oil | I-47 |
| 48 | $CH_2$ | $-CH(CH_3)_2$ | 4-BnO-C₆H₄- | $-C_2H_5$ | $-CH_3$ | mp 55–56° C. | I-48 |
| 49 | $CH_2$ | $-CH(CH_3)_2$ | 4-BnO-C₆H₄- | $-CH_2$-C₆H₅ | $-CH_3$ | oil | I-49 |

TABLE 4

| Example No. | X | $R^1$ | $R^2$ | $R^3$ | $R^4$ | mp (°C.) | Compound No. |
|---|---|---|---|---|---|---|---|
| 50 | $CH_2$ | $-CH(CH_3)_2$ | 3,5-Me₂-C₆H₃- | $-CH_2$-C₆H₅ | $-CH_3$ | oil | I-50 |
| 51 | $CH_2$ | $-CH(CH_3)_2$ | 3,5-Me₂-C₆H₃- | $-C_2H_5$ | $-CH_3$ | oil | I-51 |
| 52 | $CH_2$ | $-CH(CH_3)_2$ | 4-HO-C₆H₄- | $-C_2H_5$ | $-CH_3$ | mp 225–226° C. | I-52 |
| 53 | $CH_2$ | $-CH(CH_3)_2$ | 4-HO-C₆H₄- | $-CH_2$-C₆H₅ | $-CH_3$ | mp 203–204° C. | I-53 |
| 54 | $CH_2$ | $-CH(CH_3)_2$ | C₆H₅- | $-CH(CH_3)_2$ | $-CH_3$ | oil | I-54 |

TABLE 5
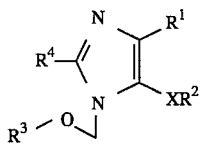
| Example No. | X | R¹ | R² | R³ | R⁴ | mp (°C.) | Compound No. |
|---|---|---|---|---|---|---|---|
| 55 | $CH_2$ | $-CH(CH_3)_2$ | 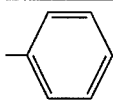 | $-CH_3$ | $-CH_3$ | oil | I-55 |
| 56 | $CH_2$ | $-CH(CH_3)_2$ | 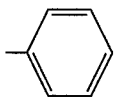 | $-CH_2CH_2CH_3$ | $-CH_3$ | oil | I-56 |
| 57 | $CH_2$ | $-CH(CH_3)_2$ | 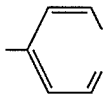 | $-C_2H_5$ | $-CH_3$ | oil | I-57 |
| 58 | $CH_2$ | $-CH(CH_3)_2$ | 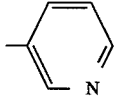 | $-C_2H_5$ | $-CH_3$ | oil | I-58 |
| 59 | $CH_2$ | $-CH(CH_3)_2$ | 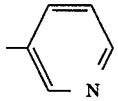 | $-CH_2$ | $-CH_3$ | oil | I-59 |
| 60 | $CH_2$ | $-CH(CH_3)_2$ | 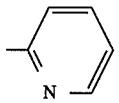 | $-C_2H_5$ | $-CH_3$ | oil | I-60 |
| 61 | $CH_2$ | $-CH(CH_3)_2$ | 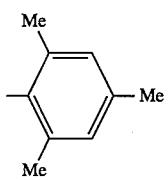 | $-CH_2$ | $-CH_3$ | mp 104–105° C. | I-61 |
TABLE 6
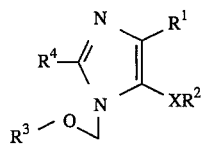
| Example No. | X | R¹ | R² | R³ | R⁴ | mp (°C.) | Compound No. |
|---|---|---|---|---|---|---|---|
| 62 | $CH_2$ | $-CH(CH_3)_2$ | 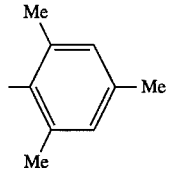 | $-C_2H_5$ | $-CH_3$ | mp 80–81° C. | I-62 |

TABLE 6-continued

[Structure: R⁴ group on imidazole with N, R¹, XR², N-O-CH₂-R³]

| Example No. | X | R¹ | R² | R³ | R⁴ | mp (°C.) | Compound No. |
|---|---|---|---|---|---|---|---|
| 63 | CH₂ | —CH(CH₃)₂ | —CH₂-phenyl | —CH₂-phenyl | —CH₃ | oil | I-63 |
| 64 | CH₂ | —CH(CH₃)₂ | —CH₂-phenyl | —C₂H₅ | —CH₃ | oil | I-64 |
| 65 | CH₂ | —CH(CH₃)₂ | 3,5-di-tBu-phenyl | —CH₂-phenyl | —CH₃ | oil | I-65 |
| 66 | CH₂ | —CH(CH₃)₂ | 3,5-di-tBu-phenyl | —C₂H₅ | —CH₃ | oil | I-66 |
| 67 | CH₂ | —CH(CH₃)₂ | 3,5-diCl-phenyl | —C₂H₅ | —CH₃ | mp 40–41° C. | I-67 |

TABLE 7

[Structure: similar with R⁴ group]

| Example No. | X | R¹ | R² | R³ | R⁴ | mp (°C.) | Compound No. |
|---|---|---|---|---|---|---|---|
| 68 | CH₂ | —CH(CH₃)₂ | 3,5-diCl-phenyl | —CH₂-phenyl | —CH₃ | oil | I-68 |

TABLE 7-continued

Structure: pyrazole with R¹, R², R³, R⁴ substituents and XR² group, $R^3-O-CH_2-N$ linkage

| Example No. | X | R¹ | R² | R³ | R⁴ | mp (°C.) | Compound No. |
|---|---|---|---|---|---|---|---|
| 69 | CH₂ | —CH(CH₃)₂ | 3,5-difluorophenyl | —CH₂—C₆H₅ (benzyl) | —CH₃ | oil | I-69 |
| 70 | CH₂ | —CH(CH₃)₂ | 3,5-difluorophenyl | —C₂H₅ | —CH₃ | oil | I-70 |

TABLE 8

| Example No. | X | R¹ | R² | R³ | R⁴ | mp (°C.) | Compound No. |
|---|---|---|---|---|---|---|---|
| 61 | CH₂ | —CH(CH₃)₂ | 2,4,6-trimethylphenyl (Me, Me, Me) | —CH₂—C₆H₅ (benzyl) | —CH₃ | oil | I-88 |
| 62 | CH₂ | —CH(CH₃)₂ | 2,4,6-trimethylphenyl (Me, Me, Me) | —C₂H₅ | —CH₃ | mp 80–81° C. | I-89 |
| 67 | CH₂ | —CH(CH₃)₂ | 3,5-dichlorophenyl | —C₂H₅ | —CH₃ | oil | I-90 |

TABLE 8-continued

[Structure: pyrimidine with $R^3-O-CH_2-N$ group, $R^1$, $R^4$, and $XR^2$ substituents]

| Example No. | X | $R^1$ | $R^2$ | $R^3$ | $R^4$ | mp (°C.) | Compound No. |
|---|---|---|---|---|---|---|---|
| 68 | $CH_2$ | $-CH(CH_3)_2$ | 3,5-dichlorophenyl | $-CH_2$-phenyl | $-CH_3$ | oil | I-91 |
| 69 | $CH_2$ | $-CH(CH_3)_2$ | 3,5-difluorophenyl | $-CH_2$-phenyl | $-CH_3$ | oil | I-92 |
| 70 | $CH_2$ | $-CH(CH_3)_2$ | 3,5-difluorophenyl | $-C_2H_5$ | $-CH_3$ | oil | I-93 |
| 71 | $CH_2$ | $-CH(CH_3)_2$ | 3,5-dimethoxyphenyl | $-CH_2$-phenyl | $-CH_3$ | oil | I-94 |
| 72 | $CH_2$ | $-CH(CH_3)_2$ | 3,5-dimethoxyphenyl | $-C_2H_5$ | $-CH_3$ | oil | I-95 |

Physicochemical properties of compounds shown in the Tables 3 to 8 above are shown below.

I-43:
$^1$H-NMR(CDCl$_3$-TMS)ppm: 1.28(d,J=7.0 Hz,6H), 2.05(s,3H) 2.42(s,3H), 2.92(m,1H), 3.39(m,2H), 4.02(m, 4H), 4.97(s,2H), 7.07–7.32(m,5H)
Elemental analysis(C$_{19}$H$_{26}$N$_2$O$_3$ 0.2H$_2$O) Calcd.:C, 68.32:H,7.97:N,8.39 Found :C,68.21:H,7.97:N,8.44

I-44:
$^1$H-NMR(CDCl$_3$-TMS)ppm: 1.08(t,J=7.0 Hz,3H), 1.29(d,J=7.0 Hz,6H), 2.44(s,3H), 2.93(m,1H), 3.30(q,J=7.0 Hz,2H), 3.99(s,2H), 4.92(s,2H), 7.07–7.32(m,5H)
Elemental analysis(C$_{17}$H$_{22}$N$_2$O 0.05) H$_2$O) Calcd.:C, 74.71:H,8.89:N,10.25 Found :C,74.64:H,8.82:N,10.20

I-45:
$^1$H-NMR(CDCl$_3$-TMS)ppm: 1.29(d,J=7.0 Hz,6H), 2.44(s,3H), 2.93(m,1H), 3.34(m,2H), 3.57(m,2H), 3.99(s, 2H), 5.00(s,2H), 7.08–7.32(m,5H)
Elemental analysis(C$_{17}$H$_{24}$N$_2$O$_2$O) Calcd.:C,70.80:H, 8.39:N,9.71 Found :C,70.71:H,8.41:N,9.67

I-46:
$^1$H-NMR(CDCl$_3$-TMS)ppm: 1.28(d,J=6.6 Hz,6H), 2.38(s,3H), 2.91(m,1H), 3.76(s,3H), 3.89(s,2H), 4.33(s,2H), 4.96(s,2H), 6.75–7.35(m,9H)
Elemental analysis(C$_{23}$H$_{28}$N$_2$O$_2$ 0.5H$_2$O) Calcd.:C, 73.96:H,7.83:N,7.50 Found :C,73.93:H,7.76:N,7.66

I-47:
$^1$H-NMR(CDCl$_3$-TMS)ppm: 1.10(t,J=7.0 Hz,3H), 1.28(d,J=6.8 Hz, 6H), 2.42(s,3H), 2.92(m,1H), 4.91(s,2H), 3.31(q,J=7.0 Hz,2H), 3.78(s,3H), 3.92(s,2H), 6.79–7.03(m, 4H)
Elemental analysis(C$_{18}$H$_{26}$N$_2$O$_2$ 0.2H$_2$) Calcd.:C, 70.65:H,8.70:N,9.15 Found :C,70.72:H,8.55:N,9.41

I-48:
$^1$H-NMR(CDCl$_3$-TMS)ppm: 1.08(t,J=7.0 Hz,3H), 1.28(d,J=7.0 Hz,6H), 1.42(s,3H), 2.93(m,1H), 5.03(s,2H), 3.30(q,J=7.0 Hz,2H), 3.92(s,2H), 4.91(s,2H), 6.86–7.45(m, 9H)
Elemental analysis(C$_{24}$H$_{30}$N$_2$O$_2$ 0.4DMF 0.2H$_2$O) Calcd.:C,73.58:H,8.14:N,8.17 Found :C,73.73:H,8.19:N,7.89

I-49:
¹H-NMR(CDCl₃-TMS)ppm: 1.28(d,J=6.8 Hz,6H), 2.38(s,3H), 2.92(m,1H), 3.89(s,2H), 4.32(s,2H), 4.96(s,2H), 5.01(s,2H), 6.82–7.43(m,14H)
Elemental analysis(C₂₉H₃₂N₂H₂ 0.5H₂O) Calcd.:C, 77.47:H,7.40:N,6.23 Found :C,77.51:H,7.22:N,6.40

I-50:
¹H-NMR(CDCl₃-TMS)ppm: 1.29(d,J=6.6 Hz,6H), 2.22(s,6H), 2.41(s,3H), 2.93(m,1H), 3.87(s,2H), 4.34(s,2H), 4.97(s,2H), 6.62(s,1H), 7.18–7.40(m,5H)
Elemental analysis(C₂₄H₃₀N₂O 0.3H₂O) Calcd.:C, 78.35:H,8.38:N,7.61 Found :C,78.26:H,8.38:N,7.68

I-51:
¹H-NMR(CDCl₃-TMS)ppm: 1.13(t,J=7.0 Hz,3H), 1.32 (d,J=7.0 Hz,6H), 2.28(s,6H), 2.47(s,3H), 2.95(m,1H), 6.73(s,2H), 3.35(q,J=7.0 Hz,2H), 3.94(s,2H), 4.96(s,2H), 6.88(s,1H)
Elemental analysis(C₁₉H₂₈N₂O 0.4H₂O) Calcd.:C, 74.18:H,9.44:N9.11 Found :C,74.20:H,9.40:N9.05

I-52:
¹H-NMR(CDCl₃-TMS)ppm: 1.10(t,J=7.0 Hz,3H), 1.29 (d,J=6.6 Hz,6H), 2.44(s,3H), 2.95(m,1H), 3.31(q,J=7.0 Hz,2H), 3.92(s,2H), 4.92(s,2H), 6.74–6.93(m,4H)
Elemental analysis(C₁₇H₂₄N₂O₂ 0.1H₂O) Calcd.:C, 70.36:H,8.41:N,9.65 Found.:C,70.38:N,8.37:H,9.62

I-53:
¹H-NMR(CD₃OD-TMS)ppm: 1.22(d,J=6.6 Hz,6H), 2.33(s,3H), 2.91(m,1H), 3.86(s,2H), 4.35(s,2H), 5.07(s,2H), 6.63–6.86(m,4H), 7.18–7.35(m,5H)
Elemental analysis(C₂₂H₂₆N₂O₂ 0.6H₂O) Calcd.:C, 73.14:H,7.59:N,7.75 Found :C,73.23:H,7.61:N,7.48

I-54:
¹H-NMR(CDCl₃-TMS)ppm: 1.05(d,J=6.2 Hz,6H), 1.27 (d,J=7.0 Hz,6H), 2.42(s,3H), 2.90(m,1H), 3.49(m,1H), 3.99(s,2H), 4.89(s,2H), 7.09–7.33(m,5H)
Elemental analysis(C₁₈H₂₆N₂O 0.5H₂O) Calcd.:C73.18, H9.21,N9.48 Found.:C73.31,H9.06,N9.59

I-55:
¹H-NMR(CDCl₃-TMS)ppm: 1.28(d,J=7.0 Hz,6H), 2.43(s,3H), 2.93(m,1H), 3.14(s,3H), 3.99(s,2H), 4.86(s,2H), 7.08–7.31(m,5H)

I-56:
¹H-NMR(CDCl₃-TMS)ppm: 0.83(t,J=7.4 Hz,3H), 1.28(d,J=7.2 Hz,6H), 1.45(m,2H), 2.42(s,3H), 2.92(m,1H), 3.17(q,J=6.4 Hz,2H), 3.99(s,2H), 4.91(s,2H), 7.08–7.33(m,5H)
Elemental analysis(C₁₈H₂₆N₂O 0.3H₂O) Calcd.:C, 74.09:H,9.19:N,9.60 Found.:C,74.06:H,9.20:N,9.61

I-57:
¹H-NMR(CDCl₃-TMS)ppm: 1.05(t,J=7.0 Hz,3H), 1.27 (d,J=7.2 Hz,6H), 2.44(s,3H), 2.88(m,1H), 3.31(q,J=7.0 Hz,2H), 7.04(d,J=6.2 Hz,2H), 3.99(s,2H), 4.92(s,2H), 8.50(d,J=5.S Hz,2H)

I-58:
¹H-NMR(CDCl₃-TMS)ppm: 1.06(t,J=7.0 Hz,3H), 1.28 (d,J=6.8 Hz,6H), 2.44(s,3H), 2.90(m,1H), 3.31(q,J=7.0 Hz,2H), 8.39–8.53(m,2H) 4.00(s,2H), 4.94(s,2H), 7.18–7.74(m,2H), I-59:
¹H-NMR(CDCl₃-TMS)ppm: 1.24(d,J=7.4 Hz,6H), 2.36(s,3H), 3.05(m,1H), 3.95(s,2H), 4.51(s,2H), 5.22(s,2H), 7.15–7.60(m,7H), 8.39–8.52(m,2H)

I-60:
¹H-NMR(CDCl₃-TMS)ppm: 1.05(t,J=7.0 Hz,3H),1.25(d, J=7.0 Hz, 6H), 2.42(s,3H), 2.93(m,1H), 3.33(q,J=7.0 Hz,2H), 4.16(s,2H), 5.08(s,2H), 6.95–7.62(m,3H), 8.50–8.55(m,1H)
Elemental analysis(C₁₆H₂₃N₃O 0.3H₂O) Calcd.:C, 68.93:H,8.53:N,15.07 Found :C,68.83:H,8.35:N,15.05

I-61:
¹H-NMR(CDCl₃-TMS)ppm: 1.02(d,J=7.0 Hz,6H), 2.20(s,6H), 2.26(s,3H), 2.28(m,1H), 2.37(s,3H), 3.93(s,2H), 4.35(s,2H), 5.08(s,2H), 6.83(s,2H), 7.23–7.40(m,5H)
Elemental analysis(C₂₅H₃₂N₂O 0.2H₂O) Calcd.:C, 78.99:H,8.59:N,7.37 Found :C,78.52:H,8.28:N,7.17

I-62:
¹H-NMR(CDCl₃-TMS)ppm: 1.02(d,J=6.8 Hz,6H), 1.18(t,J=7.0 Hz,3H) 2.21(s,6H), 2.21(m,1H), 2.27(s,3H), 2.45(s,3H) 3.37(q,J=7.0 Hz,2H), 3.94(s,2H), 5.03(s,2H), 6.84(s,2H)
Elemental analysis(C₂₀H₃₀N₂O 0.2H₂O) Calcd.:C, 75.52:H,9.63:N,8.81 Found :C,75.45:H,9.42:N,8.71

I-63:
1H-NMR(CDCl₃-TMS)ppm: 1.19(d,J=7.0 Hz,6H), 2.38(s,3H), 2.70–3.01(m,5H), 4.48(s,2H), 4.98(s,2H), 7.01–7.40(m,10H)
Elemental analysis(C₂₃H₂₈N₂O 0.6H₂O) Calcd.:C, 76.89:H,8.19:N,7.80 Found :C,76.74:H,8.07:N,7.80

I-64:
¹H-NMR(CDCl₃-TMS)ppm: 1.18(d,J=7.2 Hz,6H), 1.20(t,J=7.0 Hz,3H), 2.42(s,3H), 2.69–3.02(m,5H), 3.46(q, J=7.0 Hz,2H), 4.97(s,2H), 7.10–7.35(m,5H)
Elemental analysis (C₁₈H₂₆N₂O 0.6H₂O) Calcd.:C, 72.74:H,9.22:N,9.43 Found :C,72.74:H,9.00:N,9.32

I-65:
¹H-NMR(CDCl₃-TMS)ppm: 1.25(s,18H), 1.31(d,J= 7.0Hz,6H), 2.41(s,3H), 2.97(m,1H), 3.94(s,2H), 4.24(s,2H), 5.04(s,2H), 6.90(d,2H), 7.08–7.36(m,6H)
Elemental analysis (C₃₀H₄₂N₂O 0.6H₂O) Calcd.:C, 78.76:H,9.52:N,6.12 Found :C,78.67:H,9.31:N,6.15

I-66:
¹H-NMR(CDCl₃-TMS)ppm: 1.04(t,J=7.0 Hz,3H), 1.27(s, 18H), 1.34(d,J=7.0 Hz,6H), 2.50(s,3H), 3.21(q,J=7.0 Hz,2H), 3.96(s,2H), 4.99(s,2H)

I-67:
¹H-NMR(CDCl₃-TMS)ppm: 1.08(t,J=7.0 Hz,3H), 1.26 (d,J=7.2 Hz,6H), 2.43(s,3H), 2.85(m,1H), 3.33(q,J=7.0 Hz,2H), 3.94(s,2H), 4.94(s,2H), 6.98(d,J=1.6 Hz,2H), 7.20 (d,J=1.6 Hz,1H)
Elemental analysis(C₁₇H₂₂N₂OCl₂ 0.2H₂O) Calcd.:C, 59.20:H,6.55:N,8.12:C,120.56 Found :C,59.00:H,6.52:N, 8.13:C,120.58

I-68:
¹H-NMR(CDCl₃-TMS)ppm: 1.27(d,J=6,8 Hz,6H), 2.40(s,3H), 2.86(m,1H), 3.88(s,2H), 4.37(s,2H), 4.96(s,2H), 6.87–7.34(m,8H)

I-69:
¹H-NMR(CDCl₃-TMS)ppm: 1.27(d,J=6.6 Hz,6H), 2.39(s,3H), 2.88(m,1H), 3.91(s,2H), 4.38(s,2H), 4.95(s,2H), 6.50–7.22(m,8H)

I-70:
¹H-NMR(CDCl₃-TMS)ppm: 1.09(t,J=7.0 Hz,3H), 1.26 (d,J=6.S Hz,6H), 2.43(s,3H), 2.86(m,1H), 3.34(q,J=7.0 Hz,2H), 3.97(s,2H), 4.93(s,2H), 6.58–6.70(m,3H)

I-88:
¹H-NMR(CDCl₃-TMS)ppm: 1.26(d,J=7.2 Hz, 6H), 2.26(s,9H), 2.27(s,3H), 3.00(m,1H), 3.87(s,2H), 4.48(s,2H), 5.19(s,2H), 6.85(s,2H), 7.28–7.41(m,5H)

I-89:
¹H-NMR(CDCl₃-TMS)ppm: 1.19(t,J=7.0 Hz,3H), 1.26 (d,J=7.2 Hz,6H) 2.25(s,6H), 2.30(s,3H), 2.31(s,3H), 3.01(m, 1H), 3.44(q,J=7.0 Hz,2H), 3.85(s,2H), 5.13(s,2H), 6.83(s, 2H)

I-90:

$^1$H-NMR(CDCl$_3$-TMS)ppm: 1.22(t,J=7.0 Hz,3H), 1.24 (d,J=7.4 Hz,6H), 2.41(s,3H), 3.06(m,1H), 3.48(q,J=7.0 Hz, 2H), 3.89(s,2H), 5.17(s,2H), 7.07–7.15(m,3H)

I-91:

$^1$H-NMR(CDCl$_3$-TMS)ppm: 1.23(d,J=7.0 Hz,6H), 2.37(s,3H), 3.05(m,1H), 3.91(s,2H), 4.51(s,2H), 5.23(s,2H), 7.08–7.37(m,8H)

I-92

$^1$H-NMR(CDCl$_3$-TMS)ppm: 1.23(d,J=7.4 Hz,6H), 2.36(s,3H), 3.05(m,1H), 3.93(s,2H), 4.51(s,2H), 5.22 (s,2H), 6.50–7.42(m,8H)

I-93:

$^1$H-NMR(CDCl$_3$TMS)ppm: 1.24(d,J=7.4 Hz,6H), 1.24(t, J=7.0 Hz,3H) 2.41(s,3H), 3.07(m,1H), 3.48(q,J=7.0 Hz,2H), 3.92(s,2H) 5.17(s,2H), 6.52–6.78(m,3H)

I-94:

$^1$H-NMR(CDCl$_3$-TMS)ppm: 1.26(d,J=7.2 Hz,6H), 2.40(s,3H), 3.08(m,1H), 3.75(s,6H), 3.91(s,2H), 4.50(s,2H), 5.22(s,2H), 6.25–6.45(m,3H), 7.25–7.42(m,5H)

I-95:

$^1$H-NMR(CDCl$_3$-TMS)ppm: 1.20(t,J=7.0 Hz,3H), 1.26 (d,J=7.0 Hz,6H), 2.40(s,3H), 3.08(m,1H), 3.47(q,J=7.0 Hz,2H), 3.74(s,6H), 3.88(s,2H), 5.16(s,2H), 6.24–6.43(m, 3H)

Example 71

1-Benzyloxymethyl-5-(3,5-dimethoxybenzyl)-4-isopropyl-2-methylimidazole (I-71) and 1-benzyloxymethyl-4-(3,5-dimethoxybenzyl)-5-isopropyl-2-methylimidazole (I-94).

To a solution of 242 mg of 5-(3,5-dimethoxybenzyl)-4-isopropyl-2-methylimidazole (0.88 mmol) in 2.64 ml of dry tetrahydrofuran is added 38.8 mg of 60% oil suspension of sodium hydride (0.97 mmol) under ice cooling. Ten minutes later, 152 mg of benzyloxymethyl chloride (0.97 mmol) is added dropwise to the mixture and allowed to stand for 1 hour. The reaction mixture is poured onto ice water and extracted with ethyl acetate. The extract is washed with saturated brine, dried over sodium sulfate and filtered. The filtrate is concentrated in vacuo. The residue containing two types (non-polar material and polar material) of products is chromatographed, eluting with ethyl acetate and n-hexane The former eluate gives 189 mg of 1-benzyloxymethyl-5-(3,5-dimethoxybenzyl)-4-isopropyl-2-methylimidazole (I-71). Yield, 54.2%.

I-71:

$^1$H-NMR(CDCl$_3$-TMS)ppm: 1.29(d,J=7.0 Hz,6H), 2.39(s,3H), 2.93(m,1H), 3.72(s,6H), 3.90(s,2H), 4.36(s,2H), 4.99(s,2H), 6.18–6.30(m,3H), 7.19–7.40(m,5H)

Elemental analysis(C$_{24}$H$_{30}$N$_2$O$_3$ 0.3H$_2$O) Calcd.(%);C, 72.08:H,7.71:N,7.00 Found (%);C,72.43:H,8.07:N,6.56

The later eluate gives 25.0 mg of 1-benzyloxymethyl-4-(3,5-dimethoxybenzyl)-5-isopropyl-2-methylimidazole (I-94). Yield, 7.20%.

I-94:

$^1$H-NMR(CDCl$_3$-TMS)ppm: 1.26(d,J=7.2 Hz,6H), 2.40(s,3H), 3.08(m,1H), 3.75(s,6H), 3.91(s,2H), 4.50(s,2H), 5.22(s,2H), 6.25–6.45(m,3H), 7.25–7.42(m,5H)

Elemental analysis(C$_{24}$H$_{30}$N$_2$O$_3$ 1.3H$_2$O) Calcd.(%);C, 68.97:H,7.86:N,6.70 Found (%);C,68.89:H,7.64:N,6.52

Example 72

5-(3.5-Dimethoxybenzyl)-1-ethoxymethyl-4-isopropyl-2-methylimidazole (I-72) and 4-(3,5-dimethoxybenzyl)-1-ethoxymethyl-5-isopropyl-2-methylimidazole (I-95)

-continued

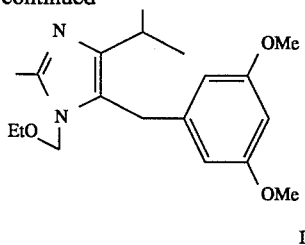

I-72

(1) Diethyl 3,5-dimethoxyacetamidomalonate 7

To a solution of 2.47 g of metallic sodium (107 mmol) in 247 ml of ethanol is added 23.28 g of diethyl acetamidomalonate (107 mmol). The resultant mixture is stirred at room temperature for 30 minutes, mixed with 20 g of 3,5-dimethoxybenzyl chloride (107 mmol), heated under reflux for 12 hours and concentrated in vacuo. The residue is extracted with ethyl acetate, washed with saturated brine, dried over sodium sulfate, and filtered. The filtrate is concentrated. The crude product is recrystallized from ethyl acetate/n-hexane to give 22.12 g of the objective diethyl 3,5-dimethoxybenzylacetamidomalonate 7. Yield, 56.18%.

7:
$^1$H-NMR(CDCl$_3$-TMS)ppm: 1.30(t,J=7.4 Hz,6H), 2.04(s, 3H), 3.73(s,6H), 3.58(s,2H), 4.28(q,J=7.2 Hz,4H), 6.15–6.35 (m,3H), 6.58(br,1H)

Elemental analysis(C$_{18}$H$_{25}$NO$_7$) Calcd.(%);C,58.85:H, 6.86:N,3.81 Found (%);C,58.67:H,6.73:N,3.82

(2) N-acetyl-3,5-dimethoxyphenylalanine 8

A mixture of 8 g of diethyl 3,5-dimethoxybenzylacetamidomalonate (21.8 mmol) and 10% aqueous Sodium hydroxide is heated under reflux for 4 hours. After cooling, the reaction mixture is mixed with 17.74 ml of 36% hydrochloric acid and heated under reflux for 30 minutes. The mixture is allowed to cool, and the precipitated crystals are filtered and dried to give 5.30 g of the objective N-acetyl-3,5-dimethoxyphenylalanine 8. Yield, 91.06%.

8:
$^1$H-NMR(CD$_3$OD-TMS)ppm: 1.91(s,3H), 3.00(m,2H), 3.74(s,6H), 4.65(m,1H), 6.30–6.40(m,3H)

Elemental analysis(C$_{13}$H$_{17}$NO$_5$ 0.3H$_2$O) Calcd.(%);C, 57.26:H,6.51:N,5.14 Found (%);C,57.09:H,6.24:N,5.13

(3) N-acetyl-3,5-dimethoxyphenylalanine methyl ester 9

To a mixture of 50 ml of 25% aqueous sodium hydroxide and 100 ml of ethyl ether is added 5 g of N-nitrosomethylurea at 10° C. and the mixture is stirred vigorously for 10 minutes. The ethyl ether layer is separated, dried over 15 g of potassium hydroxide and added to a solution of 5.3 g of N-acetyl-3,5-dimethoxyphenlalanine (19.8 mmol) in 100 ml of tetrahydrofuran, and the mixture is stirred at 10° C. for 1 hour and concentrated in vacuo. The crude product is washed with ethyl ether to give 5.16 g of the objective N-acetyl- 3,5-dimethoxyphenylalanine methyl ester 9. Yield, 92.51%.

9:
$^1$H-NMR(CDCl$_3$-TMS)ppm: 2.00(s,3H), 3.06(d,J=5.7 Hz,2H), 3.75(s,9H), 4.87(m,1H), 5.92(br,1H), 6.23–6.36(m, 3H)

Elemental analysis(C$_{14}$H$_{19}$NO$_5$ 0.2H$_2$O) Calcd.(%);C, 59.02:H,6.86:N,4.92Found (%);C,58.91:H,6.69:N,5.07

The subsequent reactions were carried out in the same manner as in Example 42 to give the objective compounds (I-72) and (I-95).

I-72:
$^1$H-NMR(CDCl$_3$-TMS) ppm: 1.11(t,J=7.0 Hz,3H), 1.28(d,J=6.6 Hz, 6H), 2.42(s,3H), 2.91(m,1H), 3.34(q,J=7.0 Hz,2H), 3.74(s,6H) 3.92(s,2H) 4.93(s,2H) 6.22–6.30(m,3H)

Examples 73–85

In examples 73 to 85, compounds (I-73)–(I-85) as shown in the following Tables 9 and 10 were prepared substantially in accordance with the procedures used for the production of compound (I-86) in Example 31.

TABLE 9

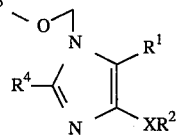

| Example No. | X | R$^1$ | R$^2$ | R$^3$ | R$^4$ | mp (°C.) | Compound No. |
|---|---|---|---|---|---|---|---|
| 73 | S | —CH$_3$ | —phenyl | —CH$_2$-phenyl | —H | oil | I-73 |
| 74 | S | —CH$_3$ | —phenyl | —CH$_2$-phenyl | —Br | oil | I-74 |
| 75 | S | —CH$_3$ | —phenyl | —CH$_2$-phenyl | —COOEt | oil | I-75 |
| 76 | S | —phenyl | —phenyl | —CH$_2$-phenyl | —H | mp 140–141° C. (HCl salt) | I-76 |

TABLE 9-continued
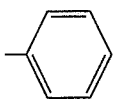
| Example No. | X | R¹ | R² | R³ | R⁴ | mp (°C.) | Compound No. |
|---|---|---|---|---|---|---|---|
| 77 | S | —CH₃ | (phenyl) | —C₂H₅ | —H | oil | I-77 |
| 78 | S | —CH₃ | —n.C₄H₉ | —CH₂(phenyl) | —H | oil | I-78 |
| 79 | S | —C₂H₅ | (phenyl) | —CH₂(phenyl) | —H | mp 90–91° C. (HNO₃ salt) | I-79 |
TABLE 10
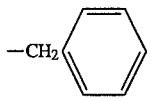
| Example No. | X | R¹ | R² | R³ | R⁴ | mp (°C.) | Compound No. |
|---|---|---|---|---|---|---|---|
| 80 | S | —H | (phenyl) | —CH₂(phenyl) | —H | mp 93° C. | I-80 |
| 81 | S | —C₂H₅ | (phenyl) | —C₂H₅ | —CH₃ | oil | I-81 |
| 82 | S | —C₂H₅ | (3,5-dimethylphenyl) | —CH₂(phenyl) | —CH₃ | oil | I-82 |
| 83 | S | —C₂H₅ | (3,5-dimethylphenyl) | —C₂H₅ | —CH₃ | oil | I-83 |

TABLE 10-continued

Structure with R¹, R², R³, R⁴, X substituents on a bicyclic core containing N-O-CH₂-R³

| Example No. | X | R¹ | R² | R³ | R⁴ | mp (°C.) | Compound No. |
|---|---|---|---|---|---|---|---|
| 84 | S | —CH(CH₃)₂ | 3,5-dimethylphenyl | —CH₂-phenyl | —CH₃ | oil | I-84 |
| 85 | S | —CH(CH₃)₂ | phenyl | —CH₂-phenyl | —CH₃ | oil | I-85 | physical properties of the compounds shown in Tables 9 and 10 are provided below.

I-73:
$^1$H-NMR(CDCl$_3$-TMS) δ ppm: 2.35(s,3H), 4.49(s,2H), 4.49(s,2H), 5.31(s,2H), 5.31(s,2H), 7.10–7.39(m,10H), 7.67(s,1H)

I-74:
$^1$H-NMR(CDCl$_3$-TMS) δ ppm: 2.37(s,3H), 4.56(s,2H), 5.37(s,2H), 7.10–7.36(m,10H)

I-75:
$^1$H-NMR(CDCl$_3$-TMS) δ ppm: 1.42(t,J=7.0 Hz,2H), 2.39(s,3H), 4.42(q,J=7.0 Hz,2H), 4.59(s,2H), 5.96(s,2H), 7.13–7.31 (m,10H)

I-76: (free base)
$^1$H-NMR(CDCl$_3$-TMS) δ ppm: 4.43(s,2H), 5.40(s,2H), 7.03–7.39 (m,13H), 7.95(s,1H), 8.06.11(m,2H)

I-77:
$^1$H-NMR(CDCl$_3$-TMS) δ ppm: 1.20(t,J=7.0 Hz,3H), 2.34(s,3H), 3.47(q,J=7.0 Hz,2H), 5.26(s,2H), 7.09–7.26(m, 5H), 7.67(s,1H)

I-78:
$^1$H-NMR(CDCl$_3$-TMS) δ ppm: 0.89(t,J=7.5 Hz,3H), 1.47(m,4H), 2.32(s,3H), 2.79(t,J=7.5 Hz,2H), 4.44(s,2H), 5.27(s,2H), 7.26–7.38(m,5H), 7.55(s,1H)

I-79: (free base)
$^1$H-NMR(CDCl$_3$-TMS) δ ppm: 1.13(t,J=7.5 Hz,3H), 2.79 (q,J=7.5 Hz,2H), 4.49(s,2H), 5.32(s,2H), 7.10–7.35(m, 10H), 7.63(s,1H)

I-80:
$^1$H-NMR(CDCl$_3$-TMS) δ ppm: 4.49(s,2H), 5.32(s,2H), 7.17–7.39 (m,11H), 7.72(s,1H)

I-81:
$^1$H-NMR(CDCl$_3$-TMS) δ ppm: 1.11(t,J=7.0 Hz,3H), 1.23 (t,J=7.0 Hz,3H), 2.48(s,3H), 2.75(q,J=7.0 Hz,2H), 3.49(q, J=7.0 Hz,2H), 5.20(s,2H), 7.00–7.30(m,5H)

I-82:
$^1$H-NMR(CDCl$_3$-TMS) δ ppm: 1.10(t,J=7.4 Hz,3H), 2.20(s,6H), 2.42(s,3H), 2.73(q,J=7.4 Hz,2H), 4.50(s,2H), 5.26(s,2H), 6.70–6.77(m,3H), 7.32–7.36(m,5H)

I-83:
$^1$H-NMR(CDCl$_3$-TMS) δ ppm: 1.12(t,J=7.6 Hz,3H), 1.22 (t,J=7.0 Hz,3H), 2.21(s,6H), 2.48(s,3H), 2.75(q,J=7.6 Hz,2H), 3.50(q,J=7.0 Hz,2H), 5.21(s,2H), 6.70.77(m,3H)

I-84:
$^1$H-NMR(CDCl$_3$-TMS) δ ppm: 1.33(d,J=7.0 Hz,6H), 2.20(s,6H), 2.40(s,3H), 3.19 (sept, 1H), 4.52(s,2H), 5.28(s, 2H), 6.60(s,2H), 7.15–7.20(m,6H)

I-85
$^1$H-NMR(CDCl$_3$-TMS) δ ppm: 1.33(d,J=7.0 Hz,6H), 2.41(s,3H), 3.18(sept,1H), 4.54(s,2H), 5.28(s,2H), 7.00–7.37(m,10H)

Compounds (I) obtained in the foregoing Examples were evaluated as to anti-retrovirus activity and cytotoxicity.

Examples 86–137

In the same manner as described above, Compounds I-96 to I-147 were prepared.

TABLE 11

| Example No. | X | R¹ | R² | R³ | R⁴ | Compound No. |
|---|---|---|---|---|---|---|
| 86 | CH₂ | —CH(CH₃)₂ | 3,5-dinitrophenyl | —CH₂-phenyl | —CH₃ | I-96 |
| 87 | CH₂ | —CH(CH₃)₂ | 3-nitrophenyl | —CH₂-phenyl | —CH₃ | I-97 |
| 88 | CH₂ | —CH(CH₃)₂ | 3,5-diaminophenyl | —CH₂-phenyl | —CH₃ | I-98 |
| 89 | CH₂ | —CH(CH₃)₂ | 3-aminophenyl | —CH₂-phenyl | —CH₃ | I-99 |
| 90 | CH₂ | —CH(CH₃)₂ | pyrimidin-5-yl | —CH₂-phenyl | —CH₃ | I-100 |
| 91 | CH₂ | —CH(CH₃)₂ | pyrazinyl | —CH₂-phenyl | —CH₃ | I-101 |
| 92 | CH₂ | —CH(CH₃)₂ | pyrimidinyl | —CH₂-phenyl | —CH₃ | I-102 |
| 93 | CH₂ | —CH(CH₃)₂ | imidazol-2-yl | —CH₂-phenyl | —CH₃ | I-103 |
| 94 | CH₂ | —CH(CH₃)₂ | imidazol-4-yl | —CH₂-phenyl | —CH₃ | I-104 |
| 95 | CH₂ | —CH(CH₃)₂ | oxazol-2-yl | —CH₂-phenyl | —CH₃ | I-105 |

TABLE 11-continued
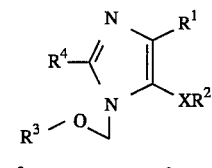
| Example No. | X | R¹ | R² | R³ | R⁴ | Compound No. |
|---|---|---|---|---|---|---|
| 96 | $CH_2$ | $-CH(CH_3)_2$ | 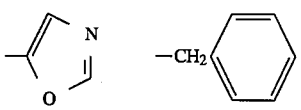 | $-CH_2$-Ph | $-CH_3$ | I-106 |
| 97 | $CH_2$ | $-CH(CH_3)_2$ | 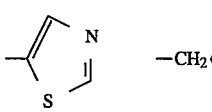 | $-CH_2$-Ph | $-CH_3$ | I-107 |
| 98 | $CH_2$ | $-CH(CH_3)_2$ | 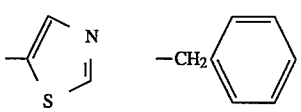 | $-CH_2$-Ph | $-CH_3$ | I-108 |
TABLE 12
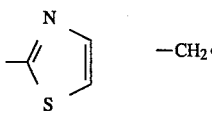
| Example No. | X | R¹ | R² | R³ | R⁴ | Compound No. |
|---|---|---|---|---|---|---|
| 99 | $CH_2$ | $-CH(CH_3)_2$ | 3,5-dinitrophenyl | $-C_2H_5$ | $-CH_3$ | I-109 |
| 100 | $CH_2$ | $-CH(CH_3)_2$ | 3-nitrophenyl | $-C_2H_5$ | $-CH_3$ | I-110 |
| 101 | $CH_2$ | $-CH(CH_3)_2$ | 3,5-diaminophenyl | $-C_2H_5$ | $-CH_3$ | I-111 |
| 102 | $CH_2$ | $-CH(CH_3)_2$ | 3-aminophenyl | $-C_2H_5$ | $-CH_3$ | I-112 |

TABLE 12-continued

| Example No. | X | R¹ | R² | R³ | R⁴ | Compound No. |
|---|---|---|---|---|---|---|
| 103 | $CH_2$ | $-CH(CH_3)_2$ | pyrimidin-5-yl | $-C_2H_5$ | $-CH_3$ | I-113 |
| 104 | $CH_2$ | $-CH(CH_3)_2$ | pyridazin-4-yl | $-C_2H_5$ | $-CH_3$ | I-114 |
| 105 | $CH_2$ | $-CH(CH_3)_2$ | pyrazin-2-yl | $-C_2H_5$ | $-CH_3$ | I-115 |
| 106 | $CH_2$ | $-CH(CH_3)_2$ | imidazol-2-yl | $-C_2H_5$ | $-CH_3$ | I-116 |
| 107 | $CH_2$ | $-CH(CH_3)_2$ | imidazol-4-yl | $-C_2H_5$ | $-CH_3$ | I-117 |
| 108 | $CH_2$ | $-CH(CH_3)_2$ | oxazol-2-yl | $-C_2H_5$ | $-CH_3$ | I-118 |
| 109 | $CH_2$ | $-CH(CH_3)_2$ | oxazol-4-yl | $-C_2H_5$ | $-CH_3$ | I-119 |
| 110 | $CH_2$ | $-CH(CH_3)_2$ | thiazol-4-yl | $-C_2H_5$ | $-CH_3$ | I-120 |
| 111 | $CH_2$ | $-CH(CH_3)_2$ | thiazol-2-yl | $-C_2H_5$ | $-CH_3$ | I-121 |

TABLE 13

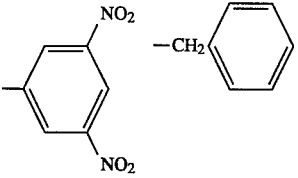

| Example No. | X | R¹ | R² | R³ | R⁴ | Compound No. |
|---|---|---|---|---|---|---|
| 112 | $CH_2$ | $-CH(CH_3)_2$ | 3,5-dinitrophenyl | $-CH_2-$phenyl | $-CH_3$ | I-122 |
| 113 | $CH_2$ | $-CH(CH_3)_2$ | 3-nitrophenyl | $-CH_2-$phenyl | $-CH_3$ | I-123 |
| 114 | $CH_2$ | $-CH(CH_3)_2$ | 3,5-diaminophenyl | $-CH_2-$phenyl | $-CH_3$ | I-124 |
| 115 | $CH_2$ | $-CH(CH_3)_2$ | 3-aminophenyl | $-CH_2-$phenyl | $-CH_3$ | I-125 |
| 116 | $CH_2$ | $-CH(CH_3)_2$ | pyrazin-2-yl | $-CH_2-$phenyl | $-CH_3$ | I-126 |
| 117 | $CH_2$ | $-CH(CH_3)_2$ | pyrimidin-4-yl | $-CH_2-$phenyl | $-CH_3$ | I-127 |
| 118 | $CH_2$ | $-CH(CH_3)_2$ | pyrimidin-2-yl | $-CH_2-$phenyl | $-CH_3$ | I-128 |
| 119 | $CH_2$ | $-CH(CH_3)_2$ | imidazol-4-yl | $-CH_2-$phenyl | $-CH_3$ | I-129 |
| 120 | $CH_2$ | $-CH(CH_3)_2$ | imidazol-5-yl | $-CH_2-$phenyl | $-CH_3$ | I-130 |
| 121 | $CH_2$ | $-CH(CH_3)_2$ | oxazol-2-yl | $-CH_2-$phenyl | $-CH_3$ | I-131 |

TABLE 13-continued
| Example No. | X | R¹ | R² | R³ | R⁴ | Compound No. |
|---|---|---|---|---|---|---|
| 122 | $CH_2$ | $-CH(CH_3)_2$ | 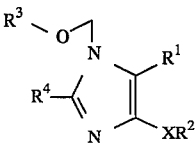 | 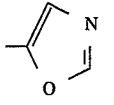 | $-CH_3$ | I-132 |
| 123 | $CH_2$ | $-CH(CH_3)_2$ | 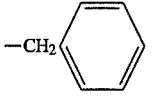 | 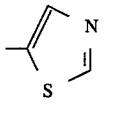 | $-CH_3$ | I-133 |
| 124 | $CH_2$ | $-CH(CH_3)_2$ | 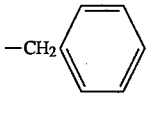 | 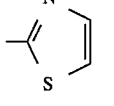 | $-CH_3$ | I-134 |
TABLE 14
| Example No. | X | R¹ | R² | R³ | R⁴ | Compound No. |
|---|---|---|---|---|---|---|
| 125 | $CH_2$ | $-CH(CH_3)_2$ | 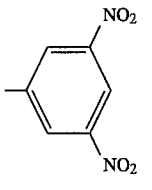 | $-C_2H_5$ | $-CH_3$ | I-135 |
| 126 | $CH_2$ | $-CH(CH_3)_2$ |  | $-C_2H_5$ | $-CH_3$ | I-136 |
| 127 | $CH_2$ | $-CH(CH_3)_2$ | 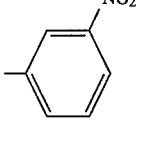 | $-C_2H_5$ | $-CH_3$ | I-137 |
| 128 | $CH_2$ | $-CH(CH_3)_2$ |  | $-C_2H_5$ | $-CH_3$ | I-138 |

TABLE 14-continued $$R^3-O-N-R^1$$
$$R^4-\overset{N}{\underset{N}{\diagup}}-XR^2$$

| Example No. | X | R¹ | R² | R³ | R⁴ | Compound No. |
|---|---|---|---|---|---|---|
| 129 | $CH_2$ | $-CH(CH_3)_2$ | 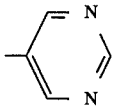 | $-C_2H_5$ | $-CH_3$ | I-139 |
| 130 | $CH_2$ | $-CH(CH_3)_2$ | 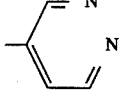 | $-C_2H_5$ | $-CH_3$ | I-140 |
| 131 | $CH_2$ | $-CH(CH_3)_2$ | 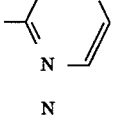 | $-C_2H_5$ | $-CH_3$ | I-141 |
| 132 | $CH_2$ | $-CH(CH_3)_2$ | 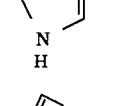 | $-C_2H_5$ | $-CH_3$ | I-142 |
| 133 | $CH_2$ | $-CH(CH_3)_2$ | 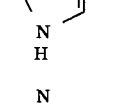 | $-C_2H_5$ | $-CH_3$ | I-143 |
| 134 | $CH_2$ | $-CH(CH_3)_2$ | 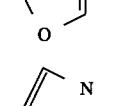 | $-C_2H_5$ | $-CH_3$ | I-144 |
| 135 | $CH_2$ | $-CH(CH_3)_2$ | 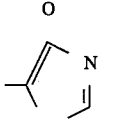 | $-C_2H_5$ | $-CH_3$ | I-145 |
| 136 | $CH_2$ | $-CH(CH_3)_2$ | 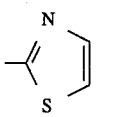 | $-C_2H_5$ | $-CH_3$ | I-146 |
| 137 | $CH_2$ | $-CH(CH_3)_2$ | 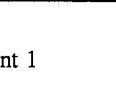 | $-C_2H_5$ | $-CH_3$ | I-147 |

Experiment 1

Infection Inhibitory Test

Anti-HIV activity and cytotoxicity were tested in the following manners.

1. Antivirus Activity (1) A human T cell MOLT-4 clone 8, a strain continuously infected with HIV (HTLV-IIIB strain), was incubated in RPMI-1640 medium containing 10% bovine fetus serum and the supernatant was isolated by filtration. After the determination of virus titer, the supernatant was stored at −80° C. A compound to be tested was diluted with the same medium to a given concentration and poured into 96-well microtiter plates by 100 μl/well. To the well was added 50 μl (2.5×10⁴ cells) MT-4 cell suspensions, followed by the addition of 50 μl [600 pfu (plaque forming unit)] HIV-containing supernatant previously diluted with the same medium.

(2) After 5-day-incubation at 37° C. in a carbon dioxide incubator, 30 μl MTT {3-(4,5-dimethylthiazol-2-yl)-2,5-diphenyltetrazolium bromide), 5 mg/ml in PBS} was added to each well, and the incubation was continued for another 1 hour, during which surviving cells reduce MTT to precipitate folmazan.

The resultant folmazan was eluted by replacing 150 μl supernatant of a culture in each well by 150 μl solution comprising 10% triton X-100 and isopropanol containing 0.4 v/v % HCl and shaking by means of a plate mixer. The resultant folmazan was assayed at OD 540 nm, and the result was evaluated by comparison with that obtained in a control test.

$IC_{50}$ is defined as a concentration of the compound (I) that gives a 50% inhibition against viral cytotoxicity.

The results are summarized in Table 15.

TABLE 15

| Compound No. | $IC_{50}$ (μg/ml) | Compound No. | $IC_{50}$ (μg/ml) |
|---|---|---|---|
| I-1 | 0.03–0.06 | I-50 | 0.016 |
| I-4 | 0.13–0.25 | I-58 | 0.5 |
| I-5 | 0.13–0.25 | I-67 | 0.005 |
| I-12 | 0.06–0.13 | I-69 | 0.003 |
| I-14 | 0.016–0.032 | I-90 | 0.5–1.0 |
| I-15 | 0.063–0.12 | I-91 | 0.5–1.0 |
| I-16 | 0.016–0.031 | I-92 | 0.25 |
| I-17 | 0.016 | I-93 | 0.06 |
| I-18 | 0.016 | AZT | 0.005–0.01 |
| I-29 | 0.13–0.25 | TIBO(R-82913) | 0.13–0.25 |
| I-42 | 0.016 | | |

2. Cytotoxicity

Cytotoxicity of a compound (I) was evaluated in a similar manner as described in 1 above except that 50 μl of the same medium is added to each well in place of the HIV-containing supernatant (viral solution).

$CC_{50}$ is defined as a concentration of the compound (I) that gives 50% cytotoxicity.

Results are summarized in Table 16 below.

TABLE 16

AZT    TIBO (R-82913)

| Compound No. | $CC_{50}$ (μg/ml) | Compound No. | $CC_{50}$ (μg/ml) |
|---|---|---|---|
| I-4 | 12.5–25 | I-50 | 6.25–12.5 |
| I-5 | 12.5–25 | I-58 | >100 |
| I-9 | 12.5–25 | I-67 | 6.25–12.5 |
| I-12 | 12.5–25 | I-69 | 6.25–12.5 |
| I-13 | 12.5–25 | I-90 | 1.0–10 |
| I-14 | 10–20 | I-91 | 10–100 |
| I-15 | 10–20 | I-92 | 6.25–12.5 |
| I-18 | 25–50 | I-93 | 12.5–25 |
| I-29 | 25–50 | AZT | 25 |
| I-42 | 3.1–6.25 | TIBO(R-82913) | 12.5–25 |

As is clear from the results of Tables 15 and 16, the compounds of the present invention or salts thereof possess anti-HIV activity, whereby the compounds of the invention; cannot only be used for the treatment of HIV virus infections such as AIDS or the like but also for the development of derivatives having improved pharmacological properties.

What we claim is:

1. A compound of the formula I:

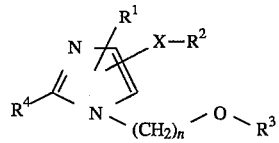

wherein:

$R^1$ is hydrogen; $C_1$–$C_{10}$ alkyl; halogen; or $C_6$–$C_{12}$ aryl which is unsubstituted or substituted by $C_1$–$C_{10}$ alkyl, halogen, nitro, amino, hydroxy, $C_1$–$C_{10}$ alkoxy or $C_7$–$C_{22}$ arylalkyloxy;

$R^2$ is selected from the group of hetero rings consisting of pyridyl; pyrimidinyl; pyridazinyl; pyrazinyl; imidazolyl; oxazolyl; and thiazolyl, each of which is unsubstituted or substituted by $C_1$–$C_{10}$ alkyl, halogen, nitro, amino, hydroxy, $C_1$–$C_{10}$ alkoxy or $C_7$–$C_{22}$ aralkyloxy;

$R^3$ is hydrogen; $C_1$–$C_{10}$ alkyl; $C_6$–$C_{12}$ aryl which is unsubstituted or substituted by $C_1$–$C_{10}$ alkyl, halogen, nitro, amino, hydroxy, $C_1$–$C_{10}$ alkoxy or $C_7$–$C_{22}$ aralkyloxy; $C_7$–$C_{22}$ aralkyl which is unsubstituted or substituted by $C_1$–$C_{10}$ alkyl, halogen, nitro, amino, hydroxy, $C_1$–$C_{10}$ alkoxy or $C_7$–$C_{22}$ aralkyloxy; or hydroxy($C_1$–$C_{10}$)alkyl which is unsubstituted or substituted by $C_6$–$C_{12}$ aryl, $C_1$–$C_{10}$ alkyl, $C_7$–$C_{22}$ aralkyl, benzoyl, 4-nitrobenzoyl, 4-tert-butylbenzoyl, benzenesulfonyl, toluenesulfonyl, formyl, acetyl, propionyl, butyryl or valeryl;

$R^4$ is hydrogen; $C_1C_{10}$ alkyl; halogen; benzoyl; 4-nitrobenzoyl; 4-tert-butylbenzoyl; benzenesulfonyl; toluenesulfonyl; formyl; acetyl; propionyl; butyryl; valeryl; hydroxy($C_1$–$C_{10}$)alkyl which is unsubstituted or substituted by $C_6$–$C_{12}$ aryl, $C_1$–$C_{10}$ alkyl, $C_7$–$C_{22}$ aralkyl, benzoyl, 4-nitrobenzoyl, 4-tert-butylbenzoyl, benzenesulfonyl, toluenesulfonyl, formyl, acetyl, propionyl, butyryl or valeryl; carboxyl; methoxycarbonyl; ethoxycarbonyl; tert-butoxycarbonyl; benzyloxycarbonyl; hydroxy; $C_6$–$C_{12}$ aryl; or $C_6$–$C_{12}$ arylthio;

X is S, SO, $SO_2$, $CH_2$, or Se; and n is an integer of 1 to 3, or a pharmaceutically acceptable salt thereof.

2. A compound according to claim 1, wherein:

$R^1$ is hydrogen; $C_1$–$C_4$ alkyl; halogen; or phenyl;

$R^2$ is pyridyl;

$R^3$ is $C_1$–$C_4$ alkyl; benzyl; or hydroxy($C_1$–$C_{10}$) alkyl;

$R^4$ is hydrogen; $C_1$–$C_4$ alkyl; halogen; formyl; hydroxymethyl; hydroxymethyl substituted by $C_6$–$C_{12}$ aryl, $C_1$–$C_{10}$ alkyl, $C_7$–$C_{22}$ aralkyl, benzoyl, 4-nitro-benzoyl, 4-tert-butylbenzoyl, benzenesulfonyl, toluenesulfonyl, formyl, acetyl, propionyl, butyryl or valeryl; carboxyl; methoxycarbonyl; ethoxycarbonyl; tert-butoxycarbonyl; benzyloxycarbonyl; hydroxy; or phenylthio;

X is S or $CH_2$; and n is 1, or a pharmaceutically acceptable salt thereof.

3. A pharmaceutical composition comprising an effective amount of a compound of claim 1 and a pharmaceutically acceptable carrier or excipient.

4. An antivirus composition which comprises an effective amount of a compound of claim 1 together with a pharmaceutically acceptable carrier therefor.

* * * * *